(12) United States Patent
Craig et al.

(10) Patent No.: US 6,696,408 B1
(45) Date of Patent: Feb. 24, 2004

(54) CONTULAKIN-G, ANALOGS THEREOF AND USES THEREFOR

(75) Inventors: A. Grey Craig, Solana Beach, CA (US); David Griffen, Greenville, NC (US); Baldomero M. Olivera, Salt Lake City, UT (US); Maren Watkins, Salt Lake City, UT (US); David R. Hillyard, Salt Lake City, UT (US); Julita Imperial, Salt Lake City, UT (US); Lourdes J. Cruz, Manila (PH); John D. Wagstaff, Satl Lake City, UT (US); Richard T. Layer, Sandy, UT (US); Robert M. Jones, Salt Lake City, UT (US); R. Tyler McCabe, Salt Lake City, UT (US)

(73) Assignees: University of Utah Research Foundation, Salt Lake City, UT (US); Cognetix, Inc., Salt Lake City, UT (US)

( * ) Notice: Subject to any disclaimer, the term of this patent is extended or adjusted under 35 U.S.C. 154(b) by 0 days.

(21) Appl. No.: 09/606,247

(22) Filed: Jun. 29, 2000

Related U.S. Application Data

(62) Division of application No. 09/420,797, filed on Oct. 19, 1999, now Pat. No. 6,369,193.
(60) Provisional application No. 60/130,661, filed on Apr. 23, 1999, provisional application No. 60/128,561, filed on Apr. 9, 1999, and provisional application No. 60/105,015, filed on Oct. 20, 1998.

(51) Int. Cl.$^7$ .......................... A01N 37/18; A61K 38/00
(52) U.S. Cl. ............................... 514/2; 514/13; 514/14; 530/324; 530/325; 530/326
(58) Field of Search ............................... 514/2, 13, 14; 530/324, 326, 325

(56) References Cited

U.S. PATENT DOCUMENTS

| | | | |
|---|---|---|---|
| 5,432,155 A | 7/1995 | Olivera et al. | 514/12 |
| 5,700,778 A | * 12/1997 | Olivera et al. | 514/12 |

OTHER PUBLICATIONS

Beers and Berkow, Eds. The Merck manual of Diagnosis and Therapy, Seventeenth Edition. Merck Research Laboratories, White House Station, N.J. 1999, pp. 1358, 1464–1467, 1531–1538, 1564–1571.*

Beers and Berkow, Eds. The Merck manual of Diagnosis and Therapy, Seventeenth Edition. Merck Research Laboratories, White House Station, N.J. 1999, pp. 312–315, 1462–1467, 1704–1711.*

Craig et al. Contulakin–G, an O–glycosylated Invertebrate Neurotensin. J. Biol. Chem. 274:20 pp. 13752–13759.*

Craig, A. G. et al. (1999). "Contulakin–G, an O–Glycosylated Invertebrate Neurotensin." *J Biol Chem* 274:13752–13759.

Vincent, J.P. et al. (1999). "Neurotensin and neurotensin receptors", *Trends Pharmacol Sci.* 20:302–309.

Shandra, O.A. et al. (1993). "[Effect of intracerebral injections of samatostatin and neurotensin on motor functions in seizure]." *Fiziol Zh* 39:76–82.

Clineschmidt, B.V. et al. (1979). "Neurotensin: antinocisponsive action in rodents." *Eur J Pharmacol* 54:129–139.

Dubuc, I. et al. (1999). "The partial agonist properties of levocabastine in neurotensin–induced analgesia." *Eur J Pharmacol* 381:9–12.

Dubuc, I. et al. (1999). "Identification of the receptor subtype involved in the analgesic effect of neurotensin." *J Neurosci* 19:503–510.

Tyler, B.M. et al. (1998). "Evidence for additional neurotensin receptor subtypes: neurotensin analogs that distinguish between neurotensin–mediated hypthermia and antinociception." *Brain Res* 792:246–252.

Kinkead, B. et al. (1999). "Does neurotensin mediate the effects of antipsychotic drugs?" *Biol Psychiatry* 46:340–351.

Nemeroff, C.B. et al. (1992). "Neurotensin, antipsychotic drugs, and schizophrenia. Basic and clinical studies." *Ann NY Acad Sci* 668:146–156.

* cited by examiner

*Primary Examiner*—Yvonne Eyler
*Assistant Examiner*—Joseph F. Murphy
(74) *Attorney, Agent, or Firm*—Rothwell, Figg, Ernst & Manbeck

(57) ABSTRACT

The present invention is directed to contulakin-G (which is the native glycosylated peptide), a des-glycosylated contulakin-G (termed Thr$_{10}$-contulakin-G), and derivatives thereof, to a cDNA clone encoding a precursor of this mature peptide and to a precursor peptide. The invention is further directed to the use of this peptide as a therapeutic for anti-seizure, anti-inflammatory, anti-shock, anti-thrombus, hypotensive, analgesia, anti-psychotic, Parkinson's disease, gastrointestinal disorders, depressive states, cognitive dysfunction, anxiety, tardive dyskinesia, drug dependency, panic attack, mania, irritable bowel syndrome, diarrhea, ulcer, GI tumors, Tourette's syndrome, Huntington's chorea, vascular leakage, anti-arteriosclerosis, vascular and vasodilation disorders, as well as neurological, neuropharmalogical and neuropsychopharmacological disorders.

4 Claims, 16 Drawing Sheets

Figure 1:
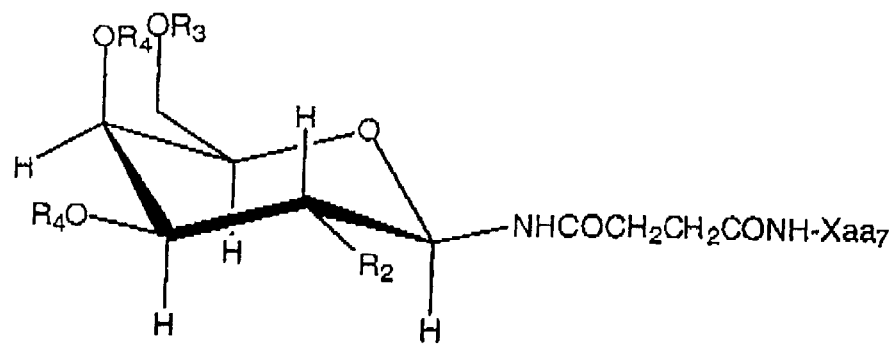

S / T - GalNAc - Gal
core 1 - $\alpha_1$, $\alpha_{1,3}$ core 2 - $\alpha_1$, $\beta_{1,6}$
S / T - GalNAc - Gal
$\beta_{1,3}$ |
GlcNAc S / T - GalNAc - GlcNAc
core 3 - $\alpha_1$, $\beta_{1,3}$ core 4 - $\alpha_1$, $\beta_{1,6}$
S / T - GalNAc - GlcNAc
$\beta_{1,3}$ |
GlcNAc S / T - GalNAc - GalNAc
core 5 - $\alpha_1$, $\alpha_{1,3}$ S / T - GalNAc - GlcNAc
core 6 - $\alpha_1$, $\beta_{1,6}$ S / T - GalNAc - GalNAc
core 7 - $\alpha_1$, $\alpha_{1,6}$ S / T - GalNAc - Gal
core 8 - $\alpha_1$, $\alpha_{1,3}$

FIG. 4

CONTULAKIN-G, ANALOGS THEREOF AND USES THEREFOR

CROSS-REFERENCE TO RELATED APPLICATIONS

The present application is a division of U.S. patent application Ser. No. 09/420,797 filed on Oct. 19, 1999, now U.S. Pat. No. 6,369,193. The present application is related to U.S. provisional patent applications Serial No. 60/105,015 filed on Oct. 20, 1998, Ser. No. 60/128,561, filed on Apr. 9, 1999 and Ser. No. 60/130,661, filed on Apr. 23, 1999, each incorporated herein by reference, and claims priority to each under 35 USC §119(e).

This invention was made with Government support under Grant No. GM-48677 awarded by the National Institutes of Health, Bethesda, Md. The United States Government has certain rights in the invention.

BACKGROUND OF THE INVENTION

The present invention is directed to contulakin-G (which is the native glycosylated peptide), a des-glycosylated contulakin-G (termed $Thr_{10}$-contulakin-G), and derivatives thereof, to a cDNA clone encoding a precursor of this mature peptide and to a precursor peptide. The invention is a further directed to the use of this peptide as a therapeutic for anti-seizure, anti-inflanmmatory, anti-shock, anti-thrombus, hypotensive, analgesia, anti-psychotic, Parkinson's disease, gastrointestinal disorders, depressive states, cognitive dysfunction, anxiety, tardive dyskinesia, drug dependency, panic attack, mania, irritable bowel syndrome, diarrhea, ulcer, GI tumors, Tourette's syndrome, Huntington's chorea, vascular leakage, anti-arteriosclerosis, vascular and vasodilation disorders, as well as neurological, neuropharmalogical and neuropsychopharrnacological disorders.

The publications and other materials used herein to illuminate the background of the invention, and in particular, cases to provide additional details respecting the practice, are incorporated by reference, and for convenience are numerically referenced in the following text and respectively grouped in the appended bibliography.

Mollusks of the genus Conus produce a venom that enables them to carry out their unique predatory lifestyle. Prey are immobilized by the venom that is injected by means of a highly specialized venom apparatus, a disposable hollow tooth that functions both in the manner of a harpoon and a hypodermic needle.

Few interactions between organisms are more striking than those between a venomous animal and its envenomated victim. Venom may be used as a primary weapon to capture prey or as a defense mechanism. Many of these venoms contain molecules directed to receptors and ion channels of neuromuscular systems.

Several peptides isolated from Conus venoms have been characterized. These include the α-, μ- and ω-conotoxins which target nicotinic acetylcholine receptors, muscle sodium channels, and neuronal calcium channels, respectively (Olivera et al., 1985). Conopressins, which are vasopressin analogs, have also been identified (Cruz et al. 1987). In addition, peptides named conantokins have been isolated from *Conus geographus* and *Conus tulipa* (Mena et al., 1990; Haack et al., 1990). These peptides have unusual age-dependent physiological effects: they induce a sleep-like state in mice younger than two weeks and hyperactive behavior in mice older than 3 weeks (Haack et al., 1990). The isolation, structure and activity of K-conotoxins are described in U.S. Pat. No. 5,633,347. Recently, peptides named contryphans containing D-tryptophan residues have been isolated from *Conus radiatus* (U.S. Ser. No. 09/061, 026), and bromo-tryptophan conopeptides have been isolated from *Conus imperialis* and *Conus radiatus* (U.S. Ser. No. 08/785,534).

It is desired to identify additional conopeptides having activities of the above conopeptides, as well as conotoxin peptides having additional activities.

SUMMARY OF THE INVENTION

The present invention is directed to contulakin-G (which is the native glycosylated peptide), a des-glycosylated contulakin-G (termed $Thr_{10}$-contulakin-G), and derivatives thereof, to a cDNA clone encoding a precursor of this mature peptide and to a precursor peptide. The invention is further directed to the use of this peptide as a therapeutic for anti-seizure, anti-inflammatory, anti-shock, anti-thrombus, hypotensive, analgesia, anti-psychotic, Parkinson's disease, gastrointestinal disorders, depressive states, cognitive dysfunction, anxiety, tardive dyskinesia, drug dependency, panic attack, mania, irritable bowel syndrome, diarrhea, ulcer, GI tumors, Tourette's syndrome, Huntington's chorea, vascular leakage, anti-arteriosclerosis, vascular and vasodilation disorders, as well as neurological, neuropharmacological and neuropsychopharmacological disorders.

In one embodiment, the present invention is directed to contulakin-G, contulakin-G propeptide and nucleic acids encoding this peptide. The contulakin-G has the following formula:

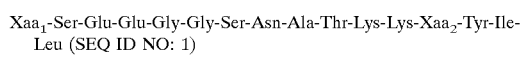

where $Xaa_1$ is pyro-Glu, $Xaa_2$ is proline or hydroxyproline and $Thr_{10}$ is modified to contain an O-glycan. $X_2$ is preferably proline. In accordance with the present invention, a glycan shall mean any N-, S- or O-linked mono-, di-, tri-, poly- or oligosaccharide that can be attached to any hydroxy, amino or thiol group of natural or modified amino acids by synthetic or enzymatic methodologies known in the art. The monosaccharides making up the glycan can include D-allose, D-altrose, D-glucose, D-mannose, D-gulose, D-idose, D-galactose, D-talose, D-galactosamine, D-glucosamine, D-N-acetyl-glucosamine (GlcNAc), D-N-acetyl-galactosamine (GalNAc), D-fucose or D-arabinose. These saccharides may be structurally modified as described herein, e.g., with one or more O-sulfate, O-phosphate, O-acetyl or acidic groups, such as sialic acid, including combinations thereof. The gylcan may also include similar polyhydroxy groups, such as D-penicillamine 2,5 and halogenated derivatives thereof or polypropylene glycol derivatives. The glycosidic linkage is beta and 1–4 or 1–3, preferably 1–3. The linkage between the glycan and the amino acid may be alpha or beta, preferably alpha and is 1–. Preferred glycans are described further herein, with the most preferred glycan being Gal(β1→3)GalNAc(α1→).

In a second embodiments the present invention is directed to a generic contulakin-G having the following general formula,

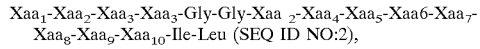

where $Xaa_1$ is pyro-Glu, Glu, Gln or γ-carboxy-Glu; $Xaa_2$ is Ser, Thr or S-glycan modified Cys; $Xaa_3$ is Glu or γ-carboxy-Glu; $Xaa_4$ is Asn, N-glycan modified Asn or S-glycan modified Cys; $Xaa_5$ is Ala or Gly; Xaa6 is Thr, Ser, S-glycan modified Cys, Tyr or any unnatural hydroxy containing amino acid (such as 4-hydroxymethyl-Phe, 4-hydroxyphenyl-Gly, 2,6-dimethyl-Tyr, 3-nitro-Tyr and 5-amino-Tyr); $Xaa_7$ is Lys, N-methyl-Lys, N,N-dimethyl-Lys, N,N,N-trimethyl-Lys, Arg, ornithine, homoarginine or any unnatural basic amino acid (such as N-1-(2-pyrazolinyl)-Arg); $Xaa_8$ is Ala, Gly, Lys, N-methyl-Lys, N,N-dimethyl-Lys, N,N,N-trimethyl-Lys, Arg, ornithine, homoarginine, any unnatural basic amino acid (such as N-1-(2-pyrazolinyl)-Arg) or X-Lys where X is $(CH_2)_n$, phenyl, $-(CH_2)_m-(CH=CH)-(CH_2)_mH$ or $-(CH_2)_m-(C\uparrow C)-(CH_2)_mH$ in which n is 1–4 and m is 0–2; $Xaa_9$ is Pro or hydroxy-Pro; and $Xaa_{10}$ is Tyr, mono-iodo-Tyr, di-iodo-Tyr, O-sulpho-Tyr, O-phospho-Tyr, nitro-Tyr, Trp, D-Trp, bromo-Trp, bromo-D-Trp, chloro-Trp, chloro-D-Trp, Phe, L-neo-Trp, any unnatural aromatic amino acid (such as nitro-Phe, 4-substituted-Phe wherein the substituent is $C_1$–$C_3$ alkyl, carboxyl, hyrdroxymethyl, sulphomethyl, halo, phenyl, $-CHO$, $-CN$, $-SO_3H$ and $-NHAc$, 2,6-dimethyl-Tyr and 5-amino-Tyr). The C-terminus contains a free carboxyl group, is amidated is acylated, contains a glycan or contains an aldehyde. It is preferred that the C-terminus contains a free carboxyl. This peptide may further contain one or more glycans as described above. The glycans may occur at residues 2, 7, 8, 10 and 16. The above and other unnatural basic amino acids, unnatural hydroxy containing amino acids or unnatural aromatic amino acids are described in Building Block Index, Version 2.2, incorporated herein by reference, by and available from RSP Amino Acid Analogues, Inc., Worcester, Mass.

Figure 12A:
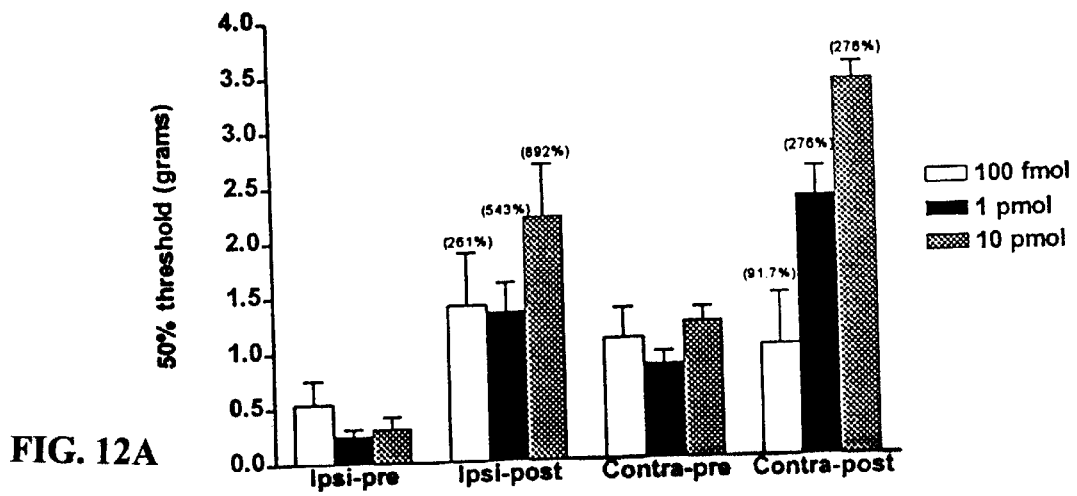
Figure 12B:
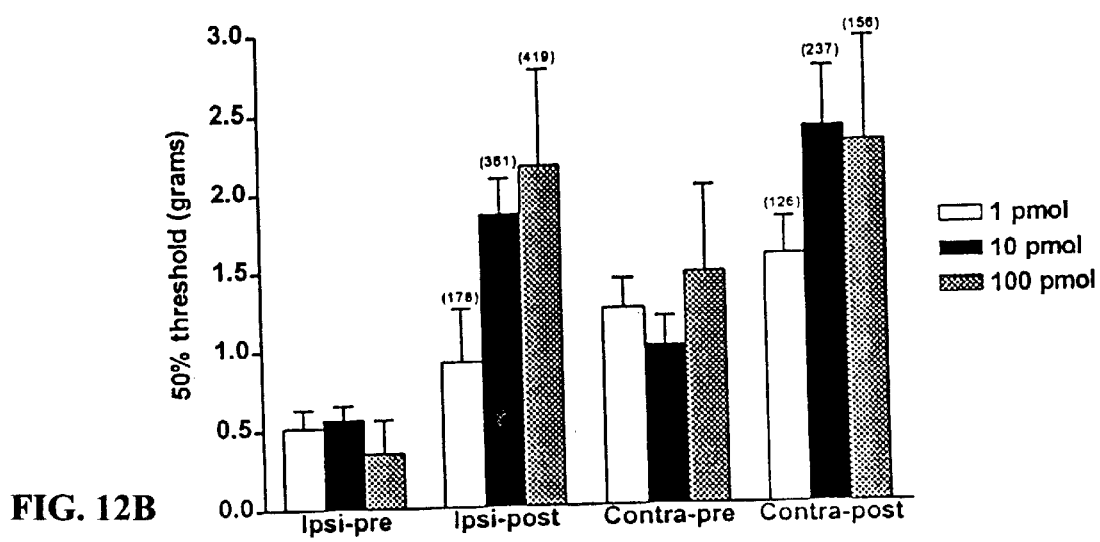
Figure 12C:
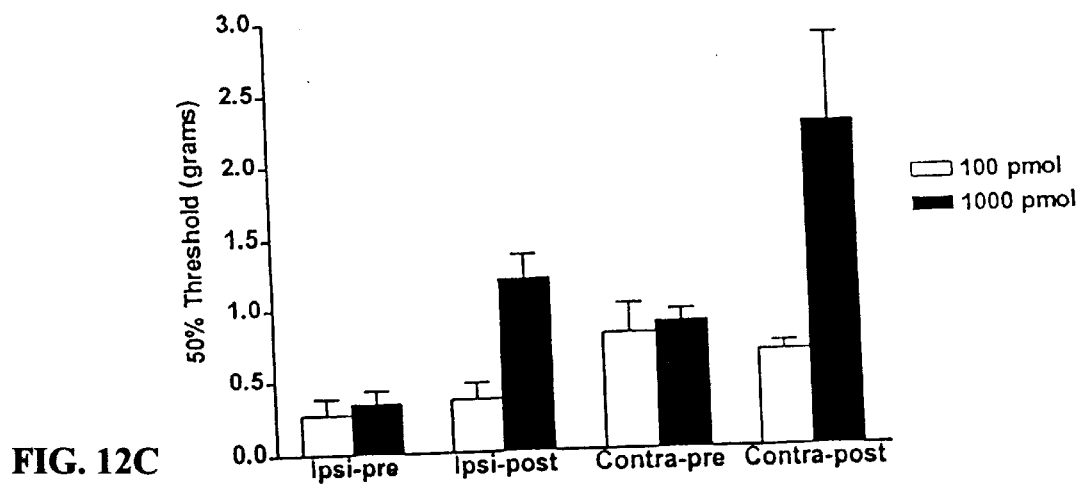

In a third embodiment, the present invention is directed to analogs of contulakin-G or the generic contulakin-G. These analogs include N-terminal truncations of contulakin-G or the generic contulakin-G up to and including $Thr_{10}$. When the N-terminal truncation is through $Thr_{10}$, $Lys_{11}$ is N-glycosylated using a carboxylated modified linker. This N-glycosylated $Lys_{11}$ can be represented as shown in FIG. 1 (Toth et al., 1999), in which $R_2$, $R_3$ and $R_4$ are as described herein. In these truncations, it is preferred that the residue proximal to the truncation is substituted with a glycosylated serine. Additional analogs include peptides in which Ser-O-glycan, Thr-O-glycan or Cys-S-glycan is substituted for a residue at position 1–9.

In a fourth embodiment, the present invention is directed to uses of the peptides described herein as a therapeutic for anti-seizure, anti-inflammatory, anti-shock, anti-thrombus, hypotensive, analgesia, anti-psychotic, Parkinson's disease, gastrointestinal disorders, depressive states, cognitive dysfunction, anxiety, tardive dyskinesia, drug dependency, panic attack, mania, irritable bowel syndrome, diarrhea, ulcer, GI tumors, Tourette's syndrome, Huntington's chorea, vascular leakage, anti-arteriosclerosis, vascular and vasodilation disorders, as well as neurological, neuropharmacological and neuropsychopharmacological disorders. In one aspect of this embodiment, analgesia is induced in a mammal using one of the peptides described herein. In a second aspect of this embodiment, epilepsy or convulsions are treated in a mammal. In a third aspect of this embodiment, schizophrenia is treated in an mammal. In a fourth aspect of this embodiment, tardive dyskinesia and acute dystonic reactions are treated in a mammal. In a fifth aspect of this embodiment, inflammation is treated in a mammal.

BRIEF DESCRIPTION OF THE FIGURES

FIG. 1 shows the structure of an N-glycosylation of Lys using a carboxylated modified linker.

FIG. 2 shows the native O-glycan attached to $Thr_{10}$ of contulakin-G.

FIG. 3 shows analogs of the glycan which can be attached to one or more residues of contulakin-G.

FIG. 4 shows the preferred core O-glycans (Van de Steen et al., 1998). Mucin type O-linked oligosaccharides are attached to Ser or Thr (or other hydroxylated residues of the present peptides) by a GalNAc residue. The monosaccharide building blocks and the linkage attached to this first GalNAc residue define the "core glycans," of which eight have been identified. The type of glycosidic linkage (orientation and connectivities) are defined for each core glycan.

FIG. 5 shows the purification of Contulakin-G. One gram of crude lyophilized venom from *Conus geographus* was extracted and applied on a Sephadex G-25 column as previously described (Olivera et al., 1984). Three successive fractions containing paralytic and sleeper activities (Ve/Vo=1.37 to 1.41) were pooled, applied on a preparative reversed phase Vydac $C_{18}$ column and eluted with a gradient of acetonitrile in 0.1% trifluroacetic acid. The component indicated by an arrow in panel A caused wobbling and death when administered icv in mice.

FIG. 6 shows a nano-ESI MS/MS spectrum (m/z 1035 precursor) of native contulakin-G (286–1886 Da) (the MS/MS experiment is denoted using a suggested shorthand (Mcluckey et al., 1991) where the closed circle represents m/z 1035 $[M+2H]^{2+}$ precursor and the arrows are directed towards the open circles which represent the fragments generated from the precursor). Above the spectrum, the structure of the glycoamino acid is represented where the arrows indicate 2 sites which lead to major fragment ions observed in the MS/MS spectrum (Craig et al., 1993).

FIGS. 7A–7C show dose-response of CGX-1063 ($Th_{10}$-contulakin-G) on spinally mediated (limb withdrawal) and supraspinally mediated (hindlimb lick) nociceptive behaviors elicited by noxious heat. Data are expressed as seconds to response (FIGS. 7A and 7B) or to first fall (FIG. 7C). In FIG. 7A, latency to the first observable response after placement on a 50° C. hotplate is shown. FIG. 7B shows latency to the first hindpaw lick. FIG. 7C shows latency to first fall after placement on the accelerating rotorod (in FIGS. 7A–7C, n=3–10).

FIGS. 8A–8B show the effect of CGX-1063 on the nociceptive response to persistent pain. In FIG. 8A, data are presented as the amount of time animals spent licking the formalin-injected hindpaw (n=7–10 animals/treatment group). Intrathecal CGX-1063 dose-dependently decreased the phase 2 nociceptive response in the formalin test compared to intrathecal saline injected controls.

FIG. 8B shows the latency to first fall from an accelerated rotorod immediately following the formalin test.

FIG. 9 shows paw withdrawal threshold to mechanical stimulation one week following partial sciatic nerve ligation. Data are presented as the 50% withdrawal threshold in grams determined with calibrated von Frey filaments (n=3–9 animals per group).

FIGS. 10A–10B show a comparison of CGX-1160 (contulakin-G), CGX- 1063 and NT in the tail-flick test. Dose-response of the three compounds is shown in FIG. 10A. FIG. 10B shows the duration of effect at the highest doses tested for each compound (CGX-1160=100 pmol; CGX-1063=100 pmol; NT=10 nmol).

FIGS. 11A–11B show the effect of CGX-1160, CGX-1063 and NT on phase 1 (FIG. 11A) and phase 2 (FIG. 11B) of the formalin test. All three of the compounds dose-dependently reduced nociceptive behavior following i.pl. formalin. In phase 2 (FIG. 11B), CGX-1160 was 10 times more potent than CGX-1063, and 600–700 times more potent than NT.

FIGS. 12A–12C show effect of CGX-1160, CGX-1063 and NT on chronic inflammation-induced mechanical allodynia. Numbers in parentheses indicate percentage of each corresponding control value. In FIG. 12A, CGX-1160 potently and dose-dependently reversed CFA-induced allodynia. In FIG. 12B, CGX- 1063 reversed CFA-induced allodynia, but was approximately 100-fold less potent in this model than CGX-1160. In FIG. 12C, NT reversed CFA-induced allodynia at 1,000 pmol, but not 100 pmol, approximately 10,000-fold less potent than CGX-1160.

Figure 13A:
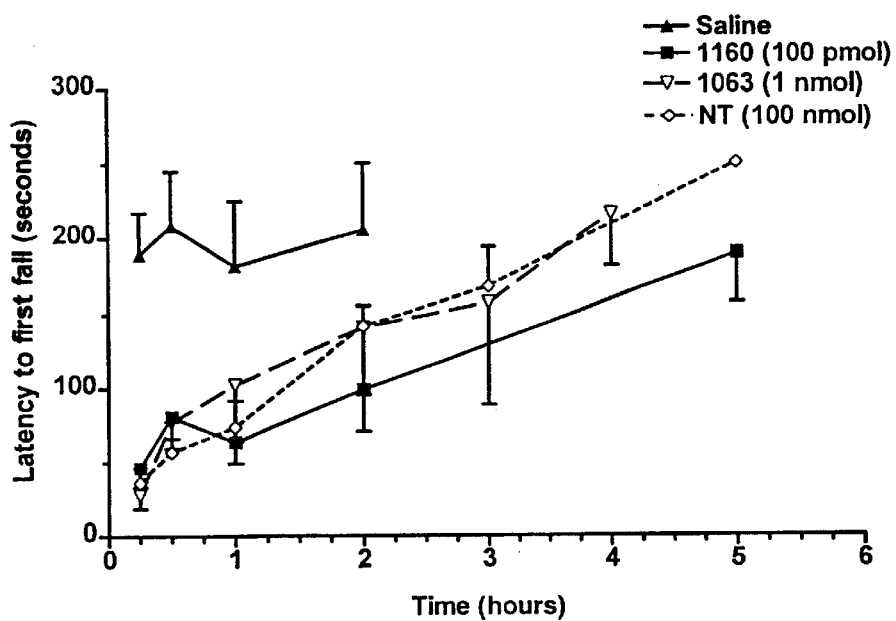
Figure 13B:
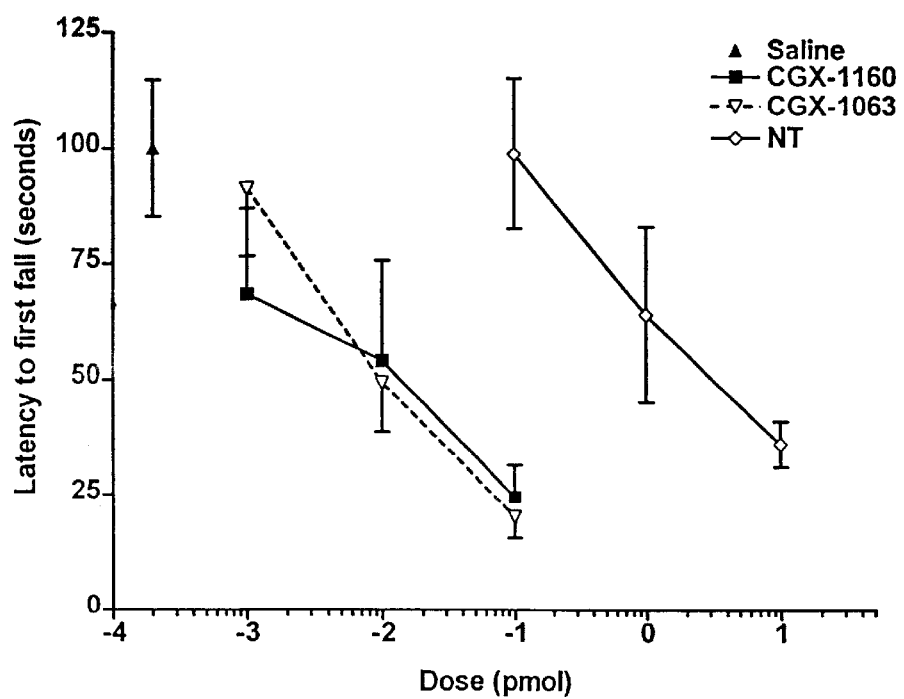

FIGS. 13A–13B show locomotor impairing effects of CGX-1160, CGX-1063 and NT. FIG. 13A shows time to peak effect and duration of effect of the three compounds at the highest doses tested (approximately 100 times the $ED_{50}$ in phase 2 of the formalin test). FIG. 13B shows dose-response of each compound on locomotor impairment.

Figure 14A:
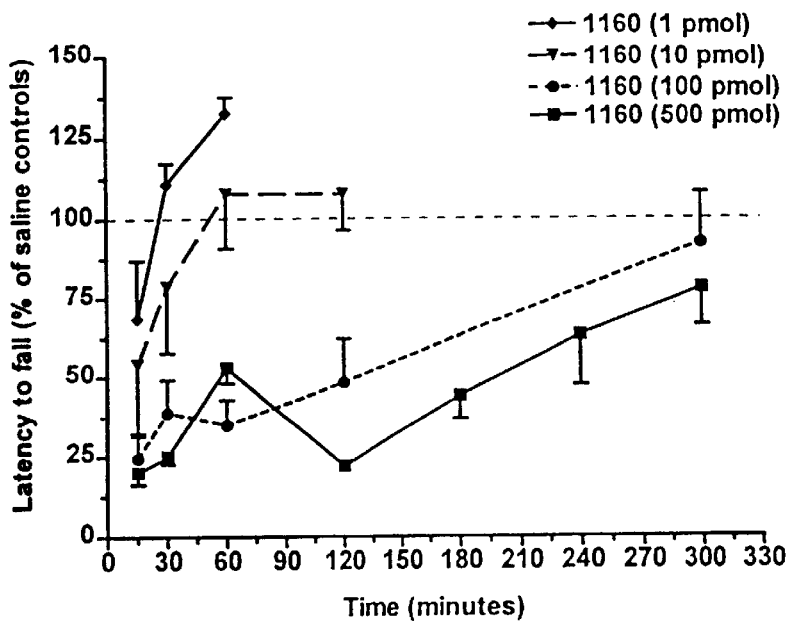
Figure 14B:
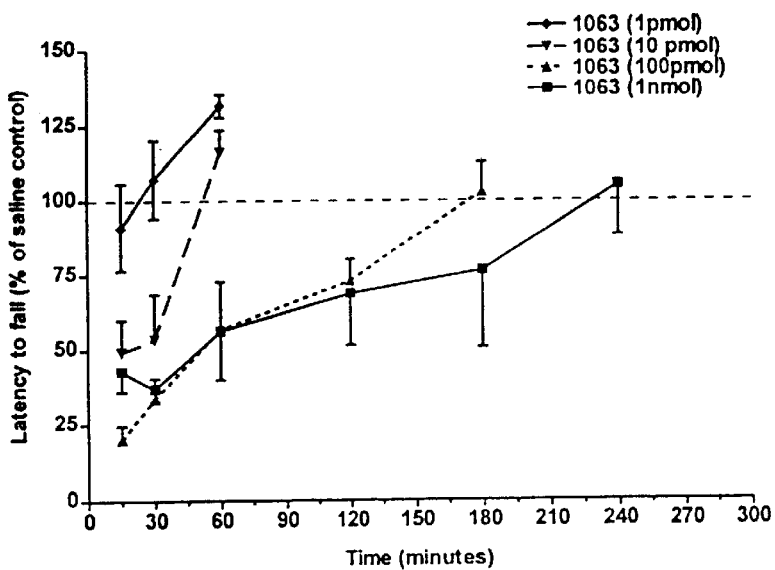
Figure 14C:
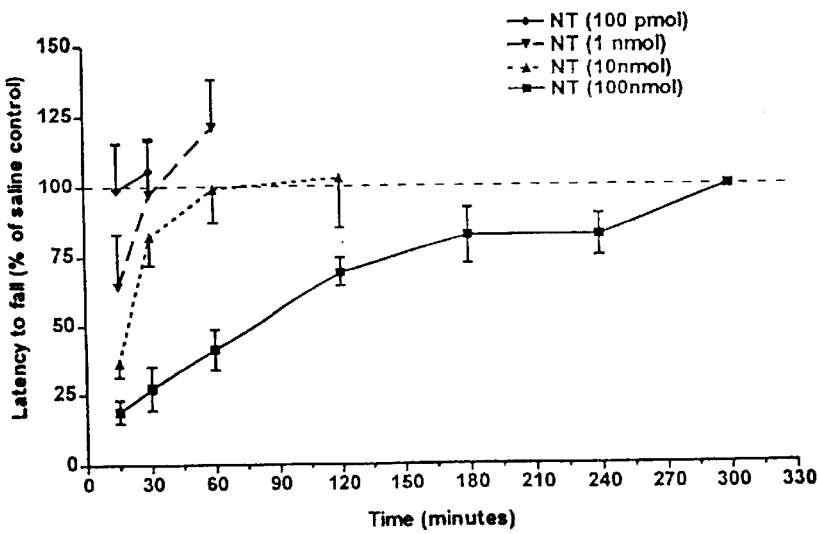

FIGS. 14A–14C show dose-effect and time to peak effect and duration of locomotor impairment of CGX-1160, CGX-1063 and NT. FIG. 14A shows that CGX- 1160 caused long-lasting motor impairment only at doses 100-fold or greater than its ED50. FIG. 14B shows that CGX-1063 caused long-last motor impairment at doses 10-fold or greater than its $ED_{50}$. FIG. 14C shows that NT caused long-last motor impairment at doses 100-fold greater than its $ED_{50}$.

Figure 15A:
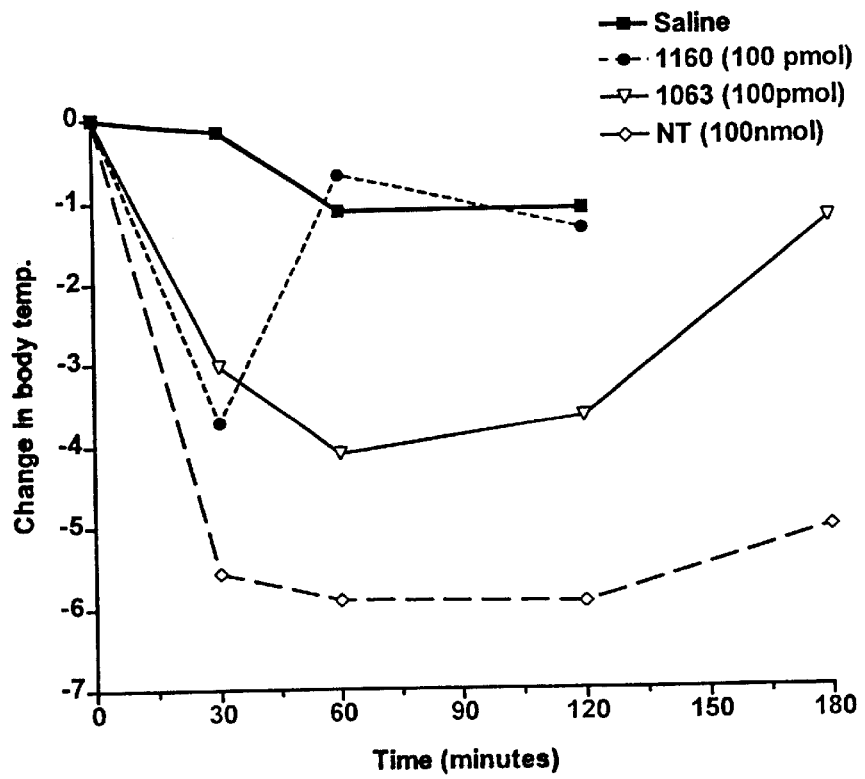
Figure 15B:
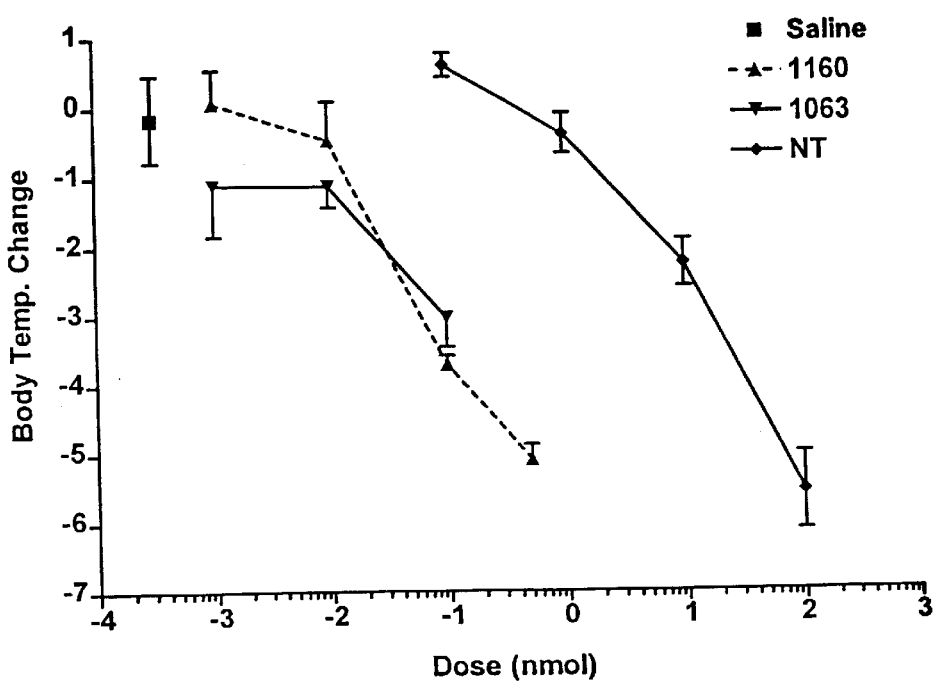

FIGS. 15A–15B show a comparison of CGX-1160, CGX-1063 and NT on change in body temperature. FIG. 15A shows time to peak effect and duration of each compound, and FIG. 15B shows dose-response of each compound.

Figure 16A:
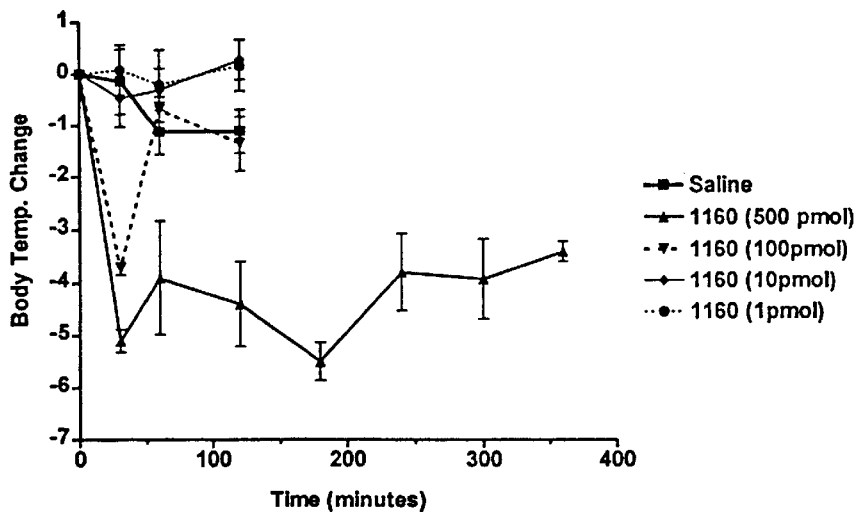
Figure 16B:
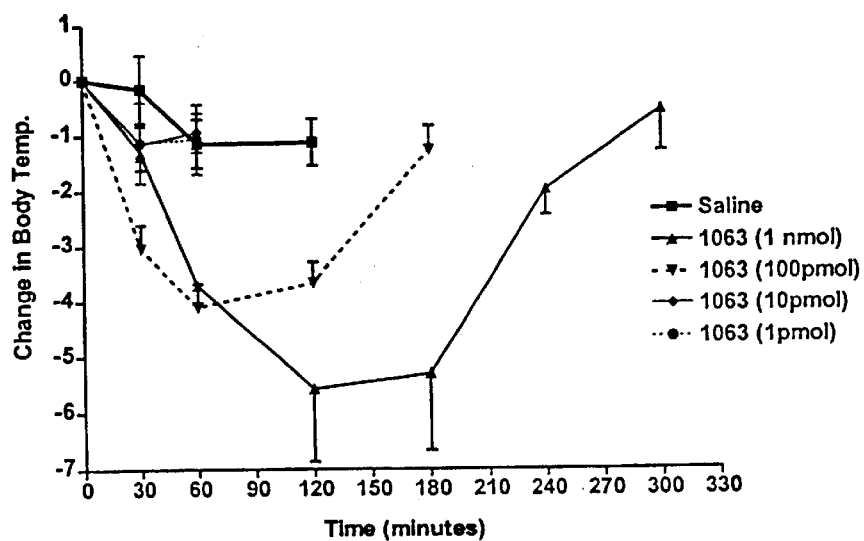
Figure 16C:
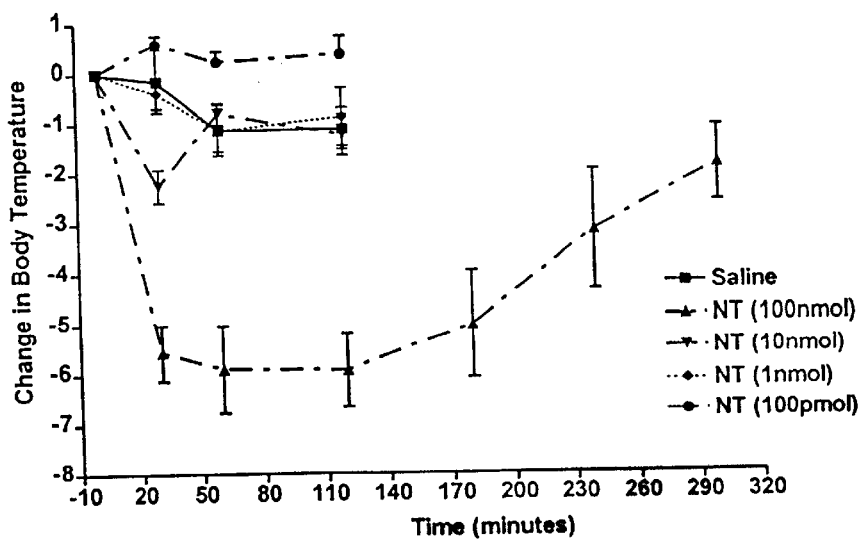

FIGS. 16A–16C show hypothermic dose-effect and duration of CGX-1160, CGX-1063 and NT. In FIG. 16A, CGX-1160 caused hypothermia only at doses 100–500 times greater than $ED_{50}$. FIG. 16B shows the long-lasting hypothermic effect of CGX-1063 at doses 10-fold higher than $ED_{50}$. (100 pmol). In FIG. 16C, NT had a hypothalamic effect at doses 10–100 times higher than its $ED_{50}$.

Figure 17:
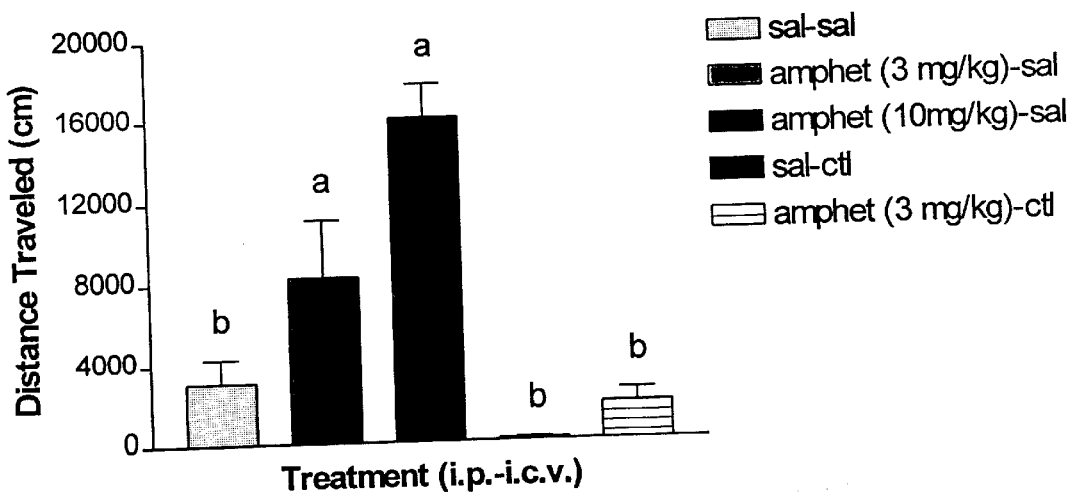

FIG. 17 shows effects of $Thr_{10}$-g Contulakin-G (CGX-1160; 100 pmol i.c.v.) on D-amphetamine-stimulated locomotor activity as measured by distance traveled. Abbreviations: sal-sal: i.p. treatment was saline, i.c.v. treatment was saline; amphet (3 mg/kg)-sal: i.p. treatment was D-amphetamine sulphate (3 mg/kg), i.c.v. treatment was saline; amphet (10 mg/kg)-sal: i.p. treatment was D-amphetamine sulphate (10 mg/kg), i.c.v. treatment was saline; sal-ctl: i.p. treatment was saline, i.c.v. treatment was $Thr_{10}$-g contulakin-G (100 pmol); amphet (3 mg/kg)-ctl: i.p. treatment was D-amphetamine sulphate (3 mg/kg), i.c.v. treatment was $Thr_{10}$-g contulakin-G (100 pmol). Each bar shows the mean±SEM of 3–7 mice per group. a: P <0.05 vs saline-saline treated group (sal-sal); b: P<0.05 vs D-amphetamine-saline group (amphet (3 mg/kg)-sal).

Figure 18:
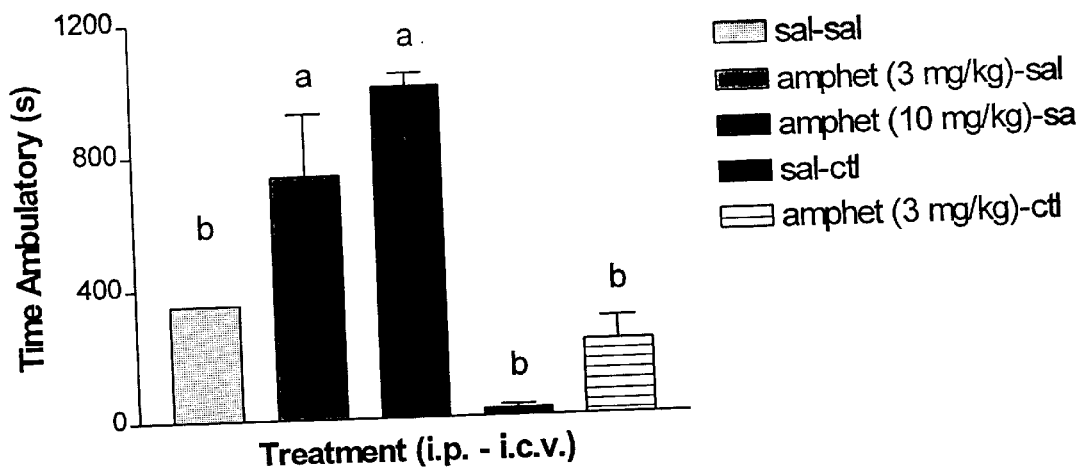

FIG. 18 shows the effects of $Thr_{10}$-g Contulakin-G (CGX-1160; 100 pmol i.c.v.) on D-amphetamine-stimulated locomotor activity as measured by time spent ambulatory (s). Abbreviations: sal-sal: i.p. treatment was saline, i.c.v. treatment was saline; amphet (3 mg/kg)-sal: i.p. treatment was D-amphetamine sulphate (3 mg/kg), i.c.v. treatment was saline; amphet (10 mg/kg)-sal: i.p. treatment was D-amphetamine sulphate (10 mg/kg), i.c.v. treatment was saline; sal-ctl: i.p. treatment was saline, i.c.v. treatment was $Thr_{10}$-g contulakin-G (100 pmol); amphet (3 mg/kg)-ctl: i.p. treatment was D-amphetamine sulphate (3 mg/kg), i.c.v. treatment was $Thr_{10}$-g contulakin-G (100 pmol). Each bar shows the mean±SEM of 3–7 mice per group. a: P<0.05 vs saline-saline treated group (sal-sal); b: P<0.05 vs D-amphetamine-saline group (amphet (3 mg/kg)-sal).

Figure 19:
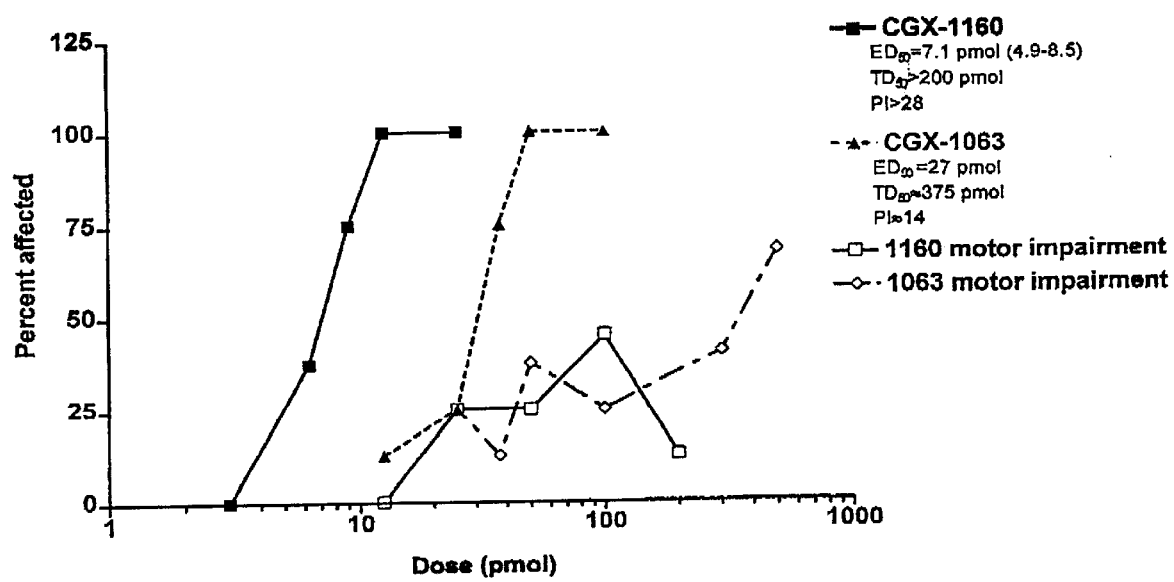

FIG. 19 shows CGX-1160 and CGX-1063 dose-dependently protect against audiogenic seizures following i.c.v. administration in Frings mice, at doses well below minimal motor impairing doses. Each point represents the percent protection (toxic in groups of at least four mice).

Figure 20:
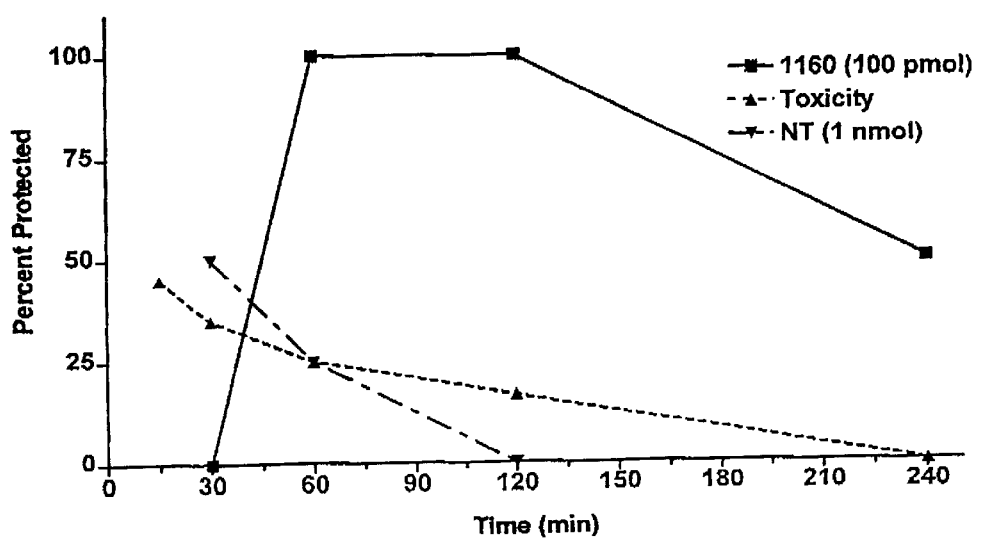

FIG. 20 shows CGX-1160's long-lasting efficacy in blocking audiogenic seizures following i.c.v. administration in Frings mice. Neurotensin is only 50% effective following i.c.v. administration of up to 5 nmol. Each point represents the percent protection in a group of four mice.

DETAILED DESCRIPTION OF THE PREFERRED EMBODIMENTS

The present invention is directed to contulakin-G (which is the native glycosylated peptide), a des-glycosylated contulakin-G (termed $Thr_{10}$-contulakin-G), and derivatives thereof, to a cDNA clone encoding a precursor of this mature peptide and to a precursor peptide. The invention is further directed to the use of this peptide as a therapeutic for anti-seizure, anti-inflammatory, anti-shock, anti-thrombus, hypotensive, analgesia, anti-psychotic, Parkinson's disease, gastrointestinal disorders, depressive states, cognitive dysfunction, anxiety, tardive dyskinesia, drug dependency, panic attack, mania, irritable bowel syndrome, diarrhea, ulcer, GI tumors, Tourette's syndrome, Huntington's chorea, vascular leakage, anti-arteriosclerosis, vascular and vasodilation disorders, as well as neurological, neuropharmalogical and neuropsychopharmacological disorders.

Figure 2:
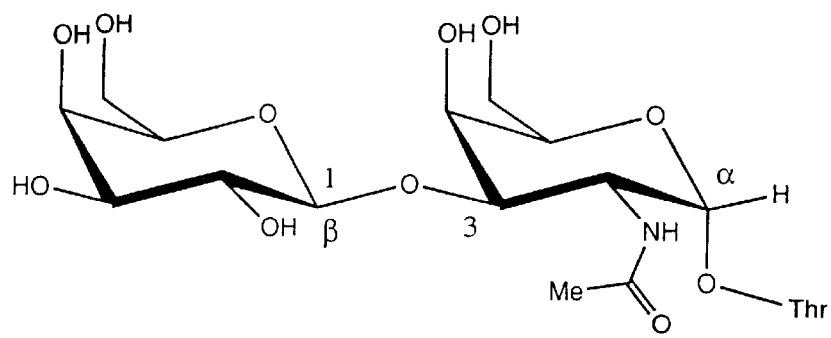
Figure 3:
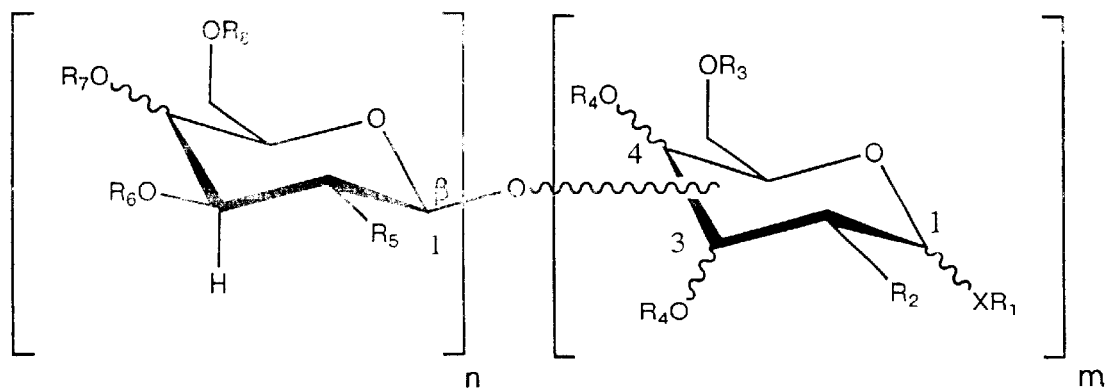

The present invention is directed to contulakin-G and contulakin-G analogues as described above. These peptides may contain single or multiple glycan post-translational modifications at one or more, up to all, of the hydroxyl sites of the peptides. The glycans are as described herein. The native O-glycan attached to contulakin-G is shown in FIG. 2. FIG. 3 shows analogs of the glycan which can be attached to one or more residues of contulakin-G. In this figure, $R_1$ is an amino capable of being derivatized with a gylcan either chemically or enzymatically; $R_2$ is OH, $NH_2$, $NHSO_3Na$, NHAc, O-sulphate, O-phosphate, or O-glycan; $R_3$ is H, $SO_3$, $PO_3$, acetyl, sialic acid or monosaccharide; $R_4$ is H, $SO_3$, $PO_3$, acetyl or monosaccharide; $R_5$ is OH, $NH_2$, $NHSO_3Na$, NHAc, O-sulphate, O-phosphate, O-monosaccharide or, O-acetyl; $R_6$ is H, $SO_3$, $PO_3$, acetyl or monosaccharide; $R_7$ is H, $SO_3$, $PO_3$, acetyl or monosaccharide; $R_8$ is H, $SO_3$, $PO_3$, acetyl or monosaccharide; n is 0–4 and m is 1–4.

The preferred core glycans which can be used to modify contulakin-G or analogs disclosed herein are shown in FIG. 4. Further branching from these cores using the monosaccharides described herein may also be made. Preferred glycosidic linkages are specified by cores 5 and 7 of FIG. 4 with further homolgation of the glycan at positions 3, 4 and 6 of the GalNAc template using the monosaccharides described herein Any free hydroxy function may be O-sulphated, O-phosphorylated or O-aceylated.

The glycosylated conopeptide (contulakin-G or CGX-1160) has higher in vivo potency than the unglycosylated conopeptide ($Thr_{10}$-contulakin-G or CGX-1063), although their in vitro potencies are about the same. The glycosylation may be important for better binding with the receptor, and/or enhanced delivery of the conopeptide to its site of action, and/or inhibition of degradation of the conopeptide.

The present invention is further directed to DNA sequence coding for contulakin-G as described in further herein. The invention is further directed to the propeptide for contulakin-G as described in further detail herein.

The present invention relates to a novel linear glycosylated contulakin-G, and derivatives thereof that are useful as pharmaceutical agents, to methods for their production, to pharmaceutical compositions which include these compounds and a pharmaceutically acceptable carrier, and to pharmaceutical methods of treatment. The novel compounds of the present invention are central nervous system agents and their biological actions are effected at a novel "Contulakin-G binding site on the neurotensin receptor". More particularly, the novel compounds of the present invention are analgesics, anti-inflammatory agents, antipsychotic agents for treating psychoses such as schizophrenia and display potent anti-seizure properties in established animal models of epilepsy.

PAIN: Chronic or intractable pain, such as may occur in conditions such as bone degenerative diseases and cancer, is a debilitating condition which is treated with a variety of analgesic agents, and often opioid compounds, such as morphine.

In general, brain pathways governing the perception of pain are still incompletely understood, sensory afferent synaptic connections to the spinal cord, termed "nociceptive pathways" have been documented in some detail. In the first leg of such pathways, C- and A- fibers which project from peripheral sites to the spinal cord carry nociceptive signals. Polysynaptic junctions in the dorsal horn of the spinal cord are involved in the relay and modulation of sensations of pain to various regions of the brain, including the periaqueductal grey region. Analgesia, or the reduction of pain perception, can be effected directly by decreasing transmission along such nociceptive pathways. Analgesic opiates are thought to act by mimicking the effects of endorphin or enkephalin peptide-containing neurons, which synapse presynaptically at the C- or A-fiber terminal and which, when they fire, inhibit release of neurotransmitters, including substance P. Descending pathways from the brain are also inhibitory on C- and A-fiber firing.

Certain types of pain have complex etiologies. For example, neuropathic pain is generally a chronic condition attributable to injury or partial transection of a peripheral nerve. This type of pain is characterized by hyperesthesia, or enhanced sensitivity to external noxious stimuli. The hyperesthetic component of neuropathic pain does not respond to the same pharmaceutical interventions as does more generalized and acute forms of pain.

Opioid compounds such as morphine, while effective in producing analgesia for many types of pain, are not always effective, and may induce tolerance in patients. When a subject is tolerant to opioid narcotics, increased doses are required to achieve a satisfactory analgesic effect. These compounds can produce side effects, such as respiratory depression, which can be life threatening. In addition, opioids frequently produce physical dependence in patients. Dependence appears to be related to the dose of opioid taken and the period of time over which it is taken by the subject. For this reason, alternate therapies for the management of chronic pain are widely sought after. In addition, compounds which serve as either a replacement for or as an adjunct to opioid treatment in order to decrease the dosage of analgesic compound required, have utility in the treatment of pain, particularly pain of the chronic, intractable type.

Since contulakin-G has been shown to act at a site on certain neurotensin receptors, and neurotensin has been shown to have analgesic actions (Clineschmidt et al. 1979), then contulakin-G like conopeptides are useful for the treatment of pain and related disorders.

SCHIZOPHRENIA: Schizophrenia is a neurogenic disorder that is currently treated primarily with neuroleptic compounds such as phenothiazines and butyrophenones, which block dopamine receptors. Since contulakin-G has been shown to act at a site on certain neurotensin receptors, and neurotensin actions are implicated in the etiology of schizophrenia (Nemeroff et al. 1992), then contulakin-G like conopeptides are useful for the treatment of schizophrenia and related disorders.

The in vitro selection criteria for conopeptides useful in treating schizophrenia, include: a) activation of Contulakin-G sites; b) high affinity reversible binding to a Contulakin-G binding site localized to the limbic region of the brain, and c) inhibition of dopamine release from brain regions, particularly limbic brain regions.

Compounds exhibiting sufficiently high activities in the above in vitro screening assays are then tested in an animal model used in screening anti-psychotic compounds.

TARDIVE DYSKINESIA AND OTHER ACUTE DYSTONIC REACTIONS: Tardive dyskinesia and acute dystonic reactions are movement disorders that are commonly produced as side effects of anti-psychotic therapy employing dopamine antagonists, such as haloperidol. These disorders are characterized by supersensitivity of dopamine receptors in certain regions of the brain associated with control of movement, particularly the basal ganglia. Currently, intermittent antipsychotic therapy is used in attempt to avoid onset of the disorder, and such disorders are treated by withdrawal of therapy.

Criteria for selection of an omega-conopeptide for treatment of tardive dyskinesia include: a) activation of Contulakin-G sites; b) high affinity reversible binding to the Contulakin-G site; c) inhibition of dopamine release from striatal brain regions, and other regions of the basal ganglia, and d) a ratio of inhibition of dopamine release in the basal ganglia to inhibition of dopamine release in the limbic regions.

Compounds showing sufficiently high activities in in vitro screening assays are then tested in the rat striatal turning model, described above. Compounds useful in the method of treating such movement disorders, when injected to the striatum on the side of the brain contralateral to the lesion, correct the turning behavior.

INFLAMMATION: A neurogenic component of inflammation has been described, in that blockade of the sympathetic nervous system, and particularly blockade of beta-adrenergic receptors, is helpful in reducing inflammatory joint damage. Compounds useful in the treatment of inflammation would be expected to have the following in vitro properties: a) activation of novel Contulakin-G sites; b) high affinity binding to the Contulakin-G binding sites, and c) inhibition of norepinephrine release from nervous tissue. Compounds exhibiting sufficiently high activities in such in vitro screening assays are tested in an animal model of rheumatoid arthritis.

EPILEPSY: Epilepsy is a general term which describes disorders of the central nervous system characterized by repeated episodes of seizures. Such seizures may involve the sensory, autonomic or motor nervous systems and are recognized electrophysiologically by the presence of abnormal electric discharges in the brain. The pathophysiology of such abnormal discharge activity is not well understood; however, there is evidence that loss of inhibitory neural input, such as GABA input, is involved in at least some epileptic seizures.

The ability of certain of the benzodiazepines (e.g., diazepam) to repress or inhibit epileptic episodes is considered by some to be evidence of a GABAergic pathophysiology in seizure activity, since these drugs are known to potentiate GABAergic neural inhibition via an effect on the GABA receptor-associated chloride ion channel. Biochemical effects of other anti-epileptic compounds include stabilization of excitable membranes by inhibition of voltage-sensitive sodium or potassium channels (phenytoin), and general depression of neuronal function characterized by facilitation of GABAergic transmission, inhibition of the effects of excitatory (glutaminergic) neurotransmission and depression of neurotransmitter release (phenobarbital).

Compounds useful in the treatment of epilepsy would be expected to have the following in vitro properties: a)activation of novel Contulakin-G sites; b) high affinity binding to the contulakin-G conopeptide binding sites, and c) inhibition of excitatory neurotransmitter release from nervous tissue. Compounds exhibiting sufficiently high activities in such in vitro screening assays fare tested in an established animal model of epilepsy.

In addition to the above specific disorders, since the peptides, derivatives and analogs of the present invention have been found to bind to the neurotensin receptor, these compounds are also useful in connection with conditions associated with the neurotensin receptor and for which neurotensin-like compounds or other compounds have been shown to be active. These activities include: methamphetamine antagonists, antipsychotic agents, cerebral medicaments, analgesic agents, anti-endotoxin shock effect, protease inhibition action (an anti-thrombin action, an anti-plasmin action), a hypotensive action, an anti-DIC action, an anti-allergic action, a wound healing action, cerebral edema, an edema of the lung, an edema of the trachea, a thrombus, an arteriosclerosis, a burn, and a hypertension, allergic diseases (such as a bronchial asthma and a pollenosis), reducing hemorrhage from a sharp trauma such as an injured tissue portion at the time of surgical operation, a lacerated wound of a brain or other tissues caused by a traffic accident and the like, and for relaxing and curing swelling, pain inflammation caused by trauma, suppressing internal hemorrhage caused by a dull trauma, edemata and inflammation which are accompanied with the internal hemorrhage, suppression and improvement of cerebral edemata by suppressing a leakage of blood components to a tissue matrix found in cerebral ischemetic diseases which include cerebral infarctions (e.g., a cerebral thrombus and a cerebral embolism), intracranial hemorrhages (e.g., a cerebral hemorrhage and a subarachnoidal hemorrhage), a transient cerebral ischemic attack, acute cerebral blood vessel disorders in a hypertensive encephalopathy, suppression and improvement of burns, chilblains, other skin inflammations and swelling, an upper tracheal inflammation, an asthma, nasal congestion, a pulmonary edema, and inflammable disorders caused by endogenous and exogenous factors, which directly damage vascular endothelia and mucous membranes, such as an environmental chemical substance, chemotherapeutics of cancer, an endotoxin, and an inflammation mediator.

The conopeptides of the present invention are identified by isolation from Conus venom. Alternatively, the conopeptides of the present invention are identified using recombinant DNA techniques by screening cDNA libraries of various Conus species using conventional techniques with degenerate probes. Clones which hybridize to these probes are analyzed to identify those which meet minimal size requirements, i.e., clones having approximately 300 nucleotides (for a propeptide), as determined using PCR primers which flank the cDNA cloning sites for the specific cDNA library being examined. These minimal-sized clones are then sequenced. The sequences are then examined for the presence of a peptide having the characteristics noted above for conopeptides. The biological activity of the peptides identified by this method is tested as described herein, in U.S. Pat. No. 5,635,347 or conventionally in the art.

These peptides are sufficiently small to be chemically synthesized. General chemical syntheses for preparing the foregoing conopeptides are described hereinafter, along with specific chemical synthesis of conopeptides and indications of biological activities of these synthetic products. Various ones of these conopeptides can also be obtained by isolation and purification from specific Conus species using the techniques described in U.S. Pat. No. 4,447,356 (Olivera et al., 1984), U.S. Pat. No. 5,514,774 (Olivera et al., 1996) and U.S. Pat. No. 5,591,821 (Olivera et al., 1997), the disclosures of which are incorporated herein by reference.

Although the conopeptides of the present invention can be obtained by purification from cone snails, because the amounts of conopeptides obtainable from individual snails are very small, the desired substantially pure conopeptides are best practically obtained in commercially valuable amounts by chemical synthesis using solid-phase strategy. For example, the yield from a single cone snail may be about 10 micrograms or less of conopeptide. By "substantially pure" is meant that the peptide is present in the substantial absence of other biological molecules of the same type; it is preferably present in an amount of at least about 85% purity and preferably at least about 95% purity. Chemical synthesis of biologically active conopeptides depends of course upon correct determination of the amino acid sequence. Thus, the conopeptides of the present invention may be isolated, synthesized and/or substantially pure.

The conopeptides can also be produced by recombinant DNA techniques well known in the art. Such techniques are described by Sambrook et al. (1989). The peptides produced in this manner are isolated, reduced if necessary, and oxidized to form the correct disulfide bonds, if present in the final molecule.

One method of forming disulfide bonds in the conopeptides of the present invention is the air oxidation of the linear peptides for prolonged periods under cold room temperatures or at room temperature. This procedure results in the creation of a substantial amount of the bioactive, disulfide-linked peptides. The oxidized peptides are fractionated using reverse-phase high performance liquid chromatography (HPLC) or the like, to separate peptides having different linked configurations. Thereafter, either by comparing these fractions with the elution of the native material or by using a simple assay, the particular fraction having the correct linkage for maximum biological potency is easily determined. It is also found that the linear peptide, or the oxidized product having more than one fraction, can sometimes be used for in vivo administration because the cross-linking and/or rearrangement which occurs in vivo has been found to create the biologically potent conopeptide molecule. However, because of the dilution resulting from the presence of other fractions of less biopotency, a somewhat higher dosage may be required.

The peptides are synthesized by a suitable method, such as by exclusively solid-phase techniques, by partial solid-phase techniques, by fragment condensation or by classical solution couplings.

In conventional solution phase peptide synthesis, the peptide chain can be prepared by a series of coupling reactions in which constituent amino acids are added to the growing peptide chain in the desired sequence. Use of various coupling reagents, e.g., dicyclohexylcarbodiimide or diisopropyl-carbonyldimidazole, various active esters, e.g., esters of N-hydroxyphthalimide or N-hydroxy-succinimide, and the various cleavage reagents, to carry out reaction in solution, with subsequent isolation and purification of intermediates, is well known classical peptide methodology. Classical solution synthesis is described in detail in the treatise, "Methoden der Organischen Chemie (Houben-Weyl): Synthese von Peptiden," (1974). Techniques of exclusively solid-phase synthesis are set forth in the textbook, "Solid-Phase Peptide Synthesis," (Stewart and Young, 1969), and are exemplified by the disclosure of U.S. Pat. No. 4,105,603 (Vale et al., 1978). The fragment condensation method of synthesis is exemplified in U.S. Pat. No. 3,972,859 (1976). Other available syntheses are exemplified by U.S. Pat. No. 3,842,067 (1974) and U.S. Pat. No. 3,862,925 (1975). The synthesis of peptides containing γ-carboxyglutamic acid residues is exemplified by Rivier et al. (1987), Nishiuchi et al. (1993) and Zhou et al. (1996). Synthesis of conopeptides have been described in U.S. Pat. No. 4,447,356 (Olivera et al., 1984), U.S. Pat. No. 5,514,774 (Olivera et al., 1996) and U.S. Pat. No. 5,591,821 (Olivera et al., 1997).

Common to such chemical syntheses is the protection of the labile side chain groups of the various amino acid moieties with suitable protecting groups which will prevent a chemical reaction from occurring at that site until the group is ultimately removed. Usually also common is the protection of an α-amino group on an amino acid or a fragment while that entity reacts at the carboxyl group, followed by the selective removal of the α-amino protecting group to allow subsequent reaction to take place at that location. Accordingly, it is common that, as a step in such a synthesis, an intermediate compound is produced which includes each of the amino acid residues located in its desired sequence in the peptide chain with appropriate side-chain protecting groups linked to various ones of the residues having labile side chains.

As far as the selection of a side chain amino protecting group is concerned, generally one is chosen which is not removed during deprotection of the α-amino groups during the synthesis. However, for some amino acids, e.g., His, protection is not generally necessary. In selecting a particular side chain protecting group to be used in the synthesis of the peptides, the following general rules are followed: (a) the protecting group preferably retains its protecting properties and is not split off under coupling conditions, (b) the protecting group should be stable under the reaction conditions selected for removing the ax-amino protecting group at each step of the synthesis, and (c) the side chain protecting group must be removable, upon the completion of the synthesis containing the desired amino acid sequence, under reaction conditions that will not undesirably alter the peptide chain.

It should be possible to prepare many, or even all, of these peptides using recombinant DNA technology. However, when peptides are not so prepared, they are preferably prepared using the Merrifield solid-phase synthesis, although other equivalent chemical syntheses known in the art can also be used as previously mentioned. Solid-phase synthesis is commenced from the C-terminus of the peptide by coupling a protected α-amino acid to a suitable resin. Such a starting material can be prepared by attaching an α-amino-protected amino acid by an ester linkage to a chloromethylated resin or a hydroxymethyl resin, or by an amide bond to a benzhydrylamine (BHA) resin or para-methylbenzhydrylamine (MBHA) resin. Preparation of the hydroxymethyl resin is described by Bodansky et al. (1966). Chloromethylated resins are commercially available from Bio Rad Laboratories (Richmond, Calif.) and from Lab. Systems, Inc. The preparation of such a resin is described by Stewart and Young (1969). BHA and MBHA resin supports are commercially available, and are generally used when the desired polypeptide being synthesized has an unsubstituted amide at the C-terminus. Thus, solid resin supports may be any of those known in the art, such as one having the formulae —O—$CH_2$-resin support, —NH BHA resin support, or —NH-MBHA resin support. When the unsubstituted amide is desired, use of a BHA or MBHA resin is preferred, because cleavage directly gives the amide. In case the N-methyl amide is desired, it can be generated from an N-methyl BHA resin. Should other substituted amides be desired, the teaching of U.S. Pat. No. 4,569,967 (Kornreich et al., 1986) can be used, or should still other groups than the free acid be desired at the C-terminus, it may be preferable to synthesize the peptide using classical methods as set forth in the Houben-Weyl text (1974).

The C-terninal amino acid, protected by Boc or Fmoc and by a side-chain protecting group, if appropriate, can be first coupled to a chloromethylated resin according to the procedure set forth in Horiki et al. (1978), using KF in DMF at about 60° C. for 24 hours with stirring, when a peptide having free acid at the C-terminus is to be synthesized. Following the coupling of the BOC-protected amino acid to the resin support, the α-amino protecting group is removed, as by using trifluoroacetic acid (TFA) in methylene chloride or TFA alone. The deprotection is carried out at a temperature between about 0° C. and room temperature. Other standard cleaving reagents, such as HCl in dioxane, and conditions for removal of specific α-amino protecting groups may be used as described in Schroder and Lubke (1965).

After removal of the α-amino-protecting group, the remaining α-amino- and side chain-protected amino acids are coupled step-wise in the desired order to obtain the intermediate compound defined hereinbefore, or as an alternative to adding each amino acid separately in the synthesis, some of them may be coupled to one another prior to addition to the solid phase reactor. Selection of an appropriate coupling reagent is within the skill of the art. Particularly suitable as a coupling reagent is N,N'-dicyclohexylcarbodiimide (DCC, DIC, HBTU, HATU, TBTU in the presence of HoBt or HoAt).

The activating reagents used in the solid phase synthesis of the peptides are well known in the peptide art. Examples of suitable activating reagents are carbodiimides, such as N,N'-diisopropylcarbodiimide and N-ethyl-N'-(3-dimethylaminopropyl)carbodiimide. Other activating reagents and their use in peptide coupling are described by Schroder and Lubke (1965) and Kapoor (1970).

Each protected amino acid or amino acid sequence is introduced into the solid-phase reactor in about a twofold or more excess, and the coupling may be carried out in a medium of dimethylformamide (DMF):$CH_2Cl_2$ (1:1) or in DMF or $CH_2Cl_2$ alone. In cases where intermediate coupling occurs, the coupling procedure is repeated before removal of the (α-amino protecting group prior to the coupling of the next amino acid. The success of the coupling reaction at each stage of the synthesis, if performed manually, is preferably monitored by the ninhydrin reaction, as described by Kaiser et al. (1970). Coupling reactions can be performed automatically, as on a Beckman 990 automatic synthesizer, using a program such as that reported in Rivier et al. (1978).

After the desired amino acid sequence has been completed, the intermediate peptide can be removed from the resin support by treatment with a reagent, such as liquid hydrogen fluoride or TFA (if using Fmoc chemistry), which not only cleaves the peptide from the resin but also cleaves all remaining side chain protecting groups and also the α-amino protecting group at the N-terminus if it was not previously removed to obtain the peptide in the form of the free acid. If Met is present in the sequence, the Boc protecting group is preferably first removed using trifluoroacetic acid (TFA)/ethanedithiol prior to cleaving the peptide from the resin with HF to eliminate potential S-alkylation. When using hydrogen fluoride or TFA for cleaving, one or more scavengers such as anisole, cresol, dimethyl sulfide and methylethyl sulfide are included in the reaction vessel.

Cyclization of the linear peptide is preferably affected, as opposed to cyclizing the peptide while a part of the peptido-resin, to create bonds between Cys residues. To effect such a disulfide cyclizing linkage, fully protected peptide can be cleaved from a hydroxymethylated resin or a chloromethylated resin support by ammonolysis, as is well known in the art, to yield the fully protected amide intermediate, which is thereafter suitably cyclized and deprotected. Alternatively, deprotection, as well as cleavage of the peptide from the above resins or a benzhydrylamine (BHA) resin or a methylbenzhydrylamine (MBHA), can take place at 0° C. with hydrofluoric acid (HF) or TFA, followed by oxidation as described above. A suitable method for cyclization is the method described by Cartier et al. (1996).

Muteins, analogs or active fragments, of the foregoing contulakin-G or $Thr_{10}$-g contulakin-G are also contemplated here. See, e.g., Hammerland et al (1992). Derivative muteins, analogs or active fragments of the conotoxin peptides may be synthesized according to known techniques, including conservative amino acid substitutions, such as outlined in U.S. Pat. No. 5,545,723 (see particularly col. 2, line 50 to col. 3, line 8); U.S. Pat. No. 5,534,615 (see particularly col. 19, line 45 to col. 33); and U.S. Pat. No. 5,364,769 (see particularly col. 4, line 55 to col. 7, line 26), each incorporated herein by reference.

Pharmaceutical compositions containing a compound of the present invention as the active ingredient can be prepared according to conventional pharmaceutical compounding techniques. See, for example, *Remington's Pharmaceutical Sciences*, 18th Ed. (1990, Mack Publishing Co., Easton, Pa.). Typically, an antagonistic amount of the active ingredient will be admixed with a pharmaceutically acceptable carrier. The carrier may take a wide variety of forms depending on the form of preparation desired for administration, e.g., intravenous, oral or parenteral.

For oral administration, the compounds can be formulated into solid or liquid preparations such as capsules, pills, tablets, lozenges, melts, powders, suspensions or emulsions. In preparing the compositions in oral dosage form, any of the usual pharmaceutical media may be employed, such as, for example, water, glycols, oils, alcohols, flavoring agents, preservatives, coloring agents, suspending agents, and the like in the case of oral liquid preparations (such as, for example, suspensions, elixirs and solutions); or carriers such as starches, sugars, diluents, granulating agents, lubricants, binders, disintegrating agents and the like in the case of oral solid preparations (such as, for example, powders, capsules and tablets). Because of their ease in administration, tablets and capsules represent the most advantageous oral dosage unit form, in which case solid pharmaceutical carriers are obviously employed. If desired, tablets may be sugar-coated or enteric-coated by standard techniques.

For parenteral administration, the compound may be dissolved in a pharmaceutical carrier and administered as either a solution or a suspension. Illustrative of suitable carriers are water, saline, dextrose solutions, fructose solutions, ethanol, or oils of animal, vegetative or synthetic origin. The carrier may also contain other ingredients, for example, preservatives, suspending agents, solubilizing agents, buffers and the like. When the compounds are being administered intrathecally, they may also be dissolved in cerebrospinal fluid.

Administration of the active agent according to this invention may be achieved using any suitable delivery means, including:

(a) pump (see, e.g., Annals of Pharmacotherapy, 27:912 (1993); Cancer, 41:1270 (1993); Cancer Research, 44:1698 (1984));

(b), microencapsulation (see, e.g., U.S. Pat. Nos. 4,352,883; 4,353,888; and 5,084,350);

(c) continuous release polymer implants (see, e.g., U.S. Pat. No. 4,883,666);

(d) macroencapsulation (see, e.g., U.S. Pat. Nos. 5,284,761, 5,158,881, 4,976,859 and 4,968,733 and published PCT patent applications WO92/19195, W095/05452);

(e) naked or unencapsulated cell grafts to the CNS (see, e.g., U.S. Pat. Nos. 5,082,670 and 5,618,531);

(f) injection, either subcutaneously, intravenously, intra-arterially, intramuscularly, or to other suitable site; or (g) oral administration, in capsule, liquid, tablet, pill, or prolonged release formulation.

In one embodiment of this invention, an active agent is delivered directly into the CNS, preferably to the brain ventricles, brain parenchyma, the intrathecal space or other suitable CNS location, most preferably intrathecally.

Alternatively, targeting therapies may be used to deliver the active agent more specifically to certain types of cells, by the use of targeting systems such as antibodies or cell-specific ligands. Targeting may be desirable for a variety of reasons, e.g. if the agent is unacceptably toxic, if it would otherwise require too high a dosage, or if it would not otherwise be able to enter target cells.

The active agents, which are peptides, can also be administered in a cell based delivery system in which a DNA sequence encoding an active agent is introduced into cells designed for implantation in the body of the patient, especially in the spinal cord region. Suitable delivery systems are described in U.S. Pat. No. 5,550,050 and published PCT Application Nos. WO92/19195, WO94/25503, WO95/01203, WO95/05452, WO 96/02286, WO96/02646, WO96/40871, WO96/40959 and WO97/12635. Suitable DNA sequences can be prepared synthetically for each active agent on the basis of the developed sequences and the known genetic code.

The active agent is preferably administered in a therapeutically effective amount. The actual amount administered, and the rate and time-course of administration, will depend on the nature and severity of the condition being treated. Prescription of treatment, e.g. decisions on dosage, timing, etc., is within the responsibility of general practitioners or specialists, and typically takes into account the disorder to be treated, the condition of the individual patient, the site of delivery, the method of administration and other factors known to practitioners. Examples of techniques and protocols can be found in *Remington's Pharmaceutical Sciences*. Typically, the active agents of the present invention exhibit their effect at a dosage range of from about 0.001 µg/kg to about 500 µg/kg, preferably from about 0.01 µg/kg to about 100 µg/kg, of the active ingredient, more preferably, from about 0.10 µg/kg to about 50 µg/kg, and most preferably, from about 1 μg/kg to about 10 μg/kg. A suitable dose can be administered in multiple sub-doses per day. Typically, a dose or sub-dose may contain from about 0.1 μg to about 500 μg of the active ingredient per unit dosage form. A more preferred dosage will contain from about 0.5 μg to about 100 μg of active ingredient per unit dosage form. Dosages are generally initiated at lower levels and increased until desired effects are achieved.

EXAMPLES

The present invention is further detailed in the following examples, which are offered by way of illustration and are not intended to limit the invention in any manner. Standard techniques well known in the art or the techniques specifically described below are utilized. The abbreviations used are: Bop, benzotriazoyloxy-tris (dimethyl amino) phosphonium hexafluorophosphate; Boc, tert butyloxycarbonyl; Fmoc, 9-fluoroenylmethoxy carbonyl; Gal, galactose; GalNAc, N-acetyl galactosamine; hNTR1, human neurotensin type 1 receptor; Hex, hexose; HexNAc, N-acetyl hexosarnine; icv, intra cerebroventricular; LSI, liquid secondary ionization; MALD, matrix assisted laser desorption; MS, mass spectrometry; mNTR3, mouse neurotensin type 3 receptor; nano-ESI, nano-electrospray; NMP, N-methylpyrrolidone; NMR, nuclear magnetic resonance; ppm, parts per million; rNTR1, rat neurotensin type 1 receptor; rNTR2, rat neurotensin type 2 receptor; RP-HPLC, reverse phase-high performance liquid chromatography. Amino acids are indicated by the standard three or one letter abbreviations.

Example 1

Experimental Procedures for Initial Analysis of Contulakin-G

1. Crude venom. *Conus geographus* specimens were collected from Marinduque Is. in the Philippines. The crude venom was obtained by dissection of the venom duct gland and then freeze dried and stored at −70° C.

2. Peptide purification. Freeze dried *C. geographus* venom (1 g) was extracted with 1.1% acetic acid and chromatographed on a Sephadex G-25 column eluted with 1.1% acetic acid as previously described (Olivera et al., 1984). A peptide that makes mice sluggish and unresponsive was purified by a series of RP-HPLC purifications on preparative and semi-preparative and analytical reverse phase $C_{18}$ columns. A gradient of acetonitrile in 0.1% trifluoroacetic acid was used to elute the peptide from the columns. The major species was re-purified prior to further characterization. Briefly, one gram of crude lyophilized venom from *Conus geographus* was extracted and applied on a Sephadex G-25 column as previously described (Olivera et al., 1984). Three successive fractions containing paralytic and sleeper activities (Ve/Vo=1.37 to 1.41) were pooled, applied on a preparative reversed phase Vydac $C_{18}$ column and eluted with a gradient of acetonitrile in 0.1% trifluroacetic acid (FIG. 1). The component indicated by an arrow in FIG. 1 caused wobbling and death when administered icv in mice. This was applied on a semipreparative $C_{18}$ column, eluted with 12–42% acetonitrile gradient in 0.1% trifluroacetic acid. The component which made mice unresponsive when administered icv, was further purified with an isocratic elution at 20.4% acetonitrile in 0.1% trifluroacetic acid. A mouse injected icv with an aliquot of the component had trouble righting itself in 5 min and became very sluggish within 12 min. In approximately 25–30 min, the mouse was stretched out and laid on its stomach.

3. Bioactivity. Typically, mice injected icv with the partially purified native peptide initially had trouble righting after 5 min, became sluggish after 12 min and then rested on their stomachs after 30 min. These signs were used as an assay to identify the biologically active peptide during purification.

4. Enzyme hydrolysis. Approximately 180 pmol of the peptide (6 μL) was incubated with 7 mU β-Galactosidase (bovine testes) (2 μL) in 50 of μL 50 mM citrate/phosphate buffer (pH 4.5) for 53 hr at 32° C. Approximately 60 pmol of the peptide (2 μL) was incubated with 2 mU O-glycosidase (*D iplococcus pneumoniae*) (2 μL) in 50 μL of 20 mM cacodylic acid (pH 6.0) for 19 hr at 32° C.

5. Chemical sequence and amino acid analysis. Automated chemical sequence analysis was performed on a 477A Protein Sequencer (Applied Biosystems, Foster City, Calif.). Amino acid analysis was carried out using pre-column derivatization. Approximately 500 pmol of the contulakin-G was sealed under vacuum with concentrated HCl, hydrolyzed at 110° C. for 24 hr, lyophilized and then derivatized with o-phthalaldehyde. The derivatized amino acids were then analyzed with RP-HPLC.

6. Mass spectrometry. Matrix assisted laser desorption (MALD) (Hillenkamp et al., 1993) mass spectra were measured using a 'Bruker REFLEX' (Bruker Daltonics, Billerica, Mass) time-of-flight (Cotter, 1989) mass spectrometer fitted with a gridless reflectron, an $N_2$ laser and a 100 MHz digitizer. An accelerating voltage of +31 kV and a reflector voltage between 1.16 and 30 kV were employed for the post source decay (Spengler et al., 1992) measurements. The sample (in 0.1% aqueous trifluoroacetic acid) was applied with α-cyano-4-hydroxycinnamic acid. Liquid secondary ionization (LSI) (Barber et al., 1982) mass spectra were measured using a Jeol HX110 (Jeol, Tokyo, Japan) double focusing mass spectrometer operated at 10 kV accelerating voltage, 1000 or 3000 resolution. The sample (in 0.1% aqueous trifluoroacetic acid and 25% acetonitrile) was mixed in a thioglycerol and dithiothreitol matrix. Nanoelectrospray (nano-ESI) mass spectra were measured using an Esquire ion trap mass spectrometer (Bruker Daltonics, Billerica, Mass.). The RP-HPLC purified sample, collected in 0.1% aqueous trifluoro-acetic acid and acetonitrile was diluted in methanol 1% acetic acid, transferred to a nanospray capillary and analyzed. The mass accuracy was typically better than 1000 ppm for the time-of-flight instrument, 200 ppm for the ion trap instrument and 20–100 ppm for the double focusing mass spectrometer depending on the resolving power settings of the magnetic sector instrument employed.

7. Synthesis of contulakin-G. The solid-phase glycopeptide synthesis was carried out manually using Fmoc chemistry, with t-butyl ether side chain protection for tyrosine and serine, N-t-Boc side chain protection for lysine, and t-butyl ester side chain protection for glutamic acid (protected amino acids were obtained from Bachem, Torrance, Calif.). Starting with a Wang resin, the amino acids were coupled with Bop/diisopropylethylamine/N-methylpyrrolidone/dichloro-methane (Stewart et al., 1984; LeNguyen et al., 1986) and the N-deprotections were done with N-methylpyrrolidone/piperidine (Stewart et al., 1984; LeNguyen et al., 1986). The Wang resin was prepared at The Salk Institute with a substitution of 0.2 nmol/g. After coupling of the first six amino acids, the resin was coupled with peracetylated Fmoc-Oβ-D-Galp-(1→3)-α-D-GalpNAc-(1→O)-threonine, synthesized as described elsewhere (Luning et al., 1989), followed by single coupling of the remaining nine amino acids in the sequence. Care was taken to remove acetic acid and acetate impurities from the glycosylated amino acids; this included chromatographic purification on silica gel using dichloromethane-ethyl acetate 4:1 as eluant, concentration and final lyophilization of the product from benzene. Non-glycosylated peptide was similarly synthesized using Fmoc-threonine (Bachem, Torrance, Calif.). The resin was subjected to cleavage conditions (95% trifluoroacetic acid/5% anisole (Stewart et al., 1984)), and in the case of the glycopeptide, the resulting peracetylated glycopeptide was isolated with RP-HPLC, the major component m/z 2322.3 (MALD analysis) corresponding to the desired product (2322.0 Da). After lyophilization, the peracetylated glycopeptide was treated with 20 $\mu$L of sodium methoxide (Sigma, St Louis, Mo.) (50 mM) in dry methanol for 1 minute (to remove O-acetyl groups on the sugar (Norberg et al., 1994)) and lyophilized at −20° C. The deacetylated sample was loaded onto a Waters Prep LC/System 500A equipped with gradient controller, Waters Model 450 Variable Wavelength Detector and Waters 1000 PrepPack cartridge chamber column (65.5×320 mm) packed with Vydac $C_{18}$ 15–20 $\mu$m particles. Flow conditions: wavelength 230 nm, AUFS 2.0, flow 100 mL/min., gradient 20–60% B/60 min; (where the A buffer was 0.1% trifluoroacetic acid in water and the B buffer was 0.1% trifluoroacetic acid in 60% aqueous acetonitrile). The fractions (200 mL) were collected manually. The major component, m/z 2069.9 (LSI analysis), corresponded to the desired product (2069.98 Da). After preparative RP-HPLC purification, sufficient purified contulakin-G was obtained for analytical characterization and biological studies. A more extensive characterization of the synthetic contulakin-G including $^1$H NMR data will be presented elsewhere.

8. Co-elution. The native and synthetic contulakin-G were analyzed separately and co-eluted with RP-HPLC, using a 2.1×150 mm Vydac $C_{18}$ column and a 0.5%/min gradient from 0% B to 40% B (where the A buffer was 0.55% trifluoroacetic acid in water and the B buffer was 0.05% trifluoroacetic acid in 90% aqueous acetonitrile).

9. Binding studies. The non-glycosylated $Thr_{10}$-contulakin-G and synthetic contulakin-G were assayed with the human neurotensin type 1 receptor (hNTR1) using a Biomek 1000 robotic workstation for all pipetting steps in the radioligand binding assays, as previously described (Cusack et al., 1993). Competition binding assays with [$^3$H] neurotensin$_{1-13}$ (1 nM) and varying concentrations of unlabeled neurotensin-$_{1-13}$, non-glycosylated $Thr_{10}$-contulakin-G or synthetic contulakin-G were carried out with membrane preparations from HEK-293 cell line. Non-specific binding was determined with 1 $\mu$M unlabeled neurotensin$_{1-13}$ in assay tubes with a total volume of 1 mL. Incubation was at 20° C. for 30 min. The assay was routinely terminated by addition of cold 0.9% NaCl (5×1.5 mL), followed by rapid filtration through a GF/B filter strip that had been pretreated with 0.2% polyethylenimine. Details of binding assays have been described before (Cusack et al., 1991). The data were analyzed using the LIGAND program (Munson et al., 1980).

The non-glycosylated $Thr_{10}$-contulakin-G and synthetic contulakin-G were separately assayed with the rat neurotensin type 1 and type 2 receptors (rNTRI and rNTR2) and mouse neurotensin type 3 receptor (mNTR3). [$^{125}$I-Tyr ] neurotensin$_{1-13}$ was prepared and purified as previously described (Saadoul et al., 1984). Stable transfected CHO cells expressing either the rNTR1 (Tanaka et al., 1990) or the rNTR2 (cloned in the laboratory of J. Mazella by screening a rat brain cDNA library (Stratagene)) were grown in DMEM containing 10% fetal calf serum and 0.25 mg/mL G418 (Sigma, France). Cell membrane homogenates were prepared as initially described (Chabry et al., 1994). Protein concentration was determined by the Bio-Rad procedure with ovalbumin as the standard.

10. Binding experiments on cell membranes. Membranes (25 $\mu$g for NTR2 and 10 $\mu$g for NTR1) were incubated with 0.4 nM [$^{125}$I-Tyr$^3$] neurotensin$_{1-13}$ (2000 Ci/mmol) and increasing concentrations of Neurotensin$_{1-13}$, non-glycosylated $Thr_{10}$-contulakin-G or synthetic contulakin-G for 20 min at 25° C. in 250 $\mu$l of 50 mM Tris-HCl (pH 7.5) containing 0.1% bovine serum albumin and 0.8 mM 1–10-phenanthroline. Binding experiments were terminated by the addition of 2 mL of ice-cold buffer followed by filtration through cellulose acetate filters (Sartorius) and washing twice. Radioactivity retained on filters was counted with a $\gamma$-counter.

11. Binding experiments on solubilized extracts. CHAPS-solubilized extracts (100 $\mu$g) were incubated with 0.2 nM [$^{125}$I-Tyr$^3$] neurotensin$_{1-13}$ for 1 hr at 0° C. in 250 $\mu$L of Tris-glerol buffing containing 0.1% CHAPS. Bound ligand was separated from free ligand by filtration on GF/B filters pretreated with 0.3% polyethylenimine. Filters were rapidly washed twice with 3 mL of ice cold buffer and counted for radioactivity.

For binding experiments on mNTR3, membrane homogenates from mouse brain were re-suspended in 25 mM Tris-HCl buffer (pH 7.5) containing 10% (w/v) glycerol, 0.1 mM phenylmethylsulfonyl fluoride, 1 $\mu$M pepstatin, 1 mM iodoacetamide, and 5 mM EDTA (Tris-glycerol buffer). Solubilization was carried out by incubating homogenates at a concentration of 10 mg/mL in the Tris-glycerol buffer with 0.625% CHAPS containing 0.125% CHS (Mazella et al., 1988). Solubilized extracts were recovered by centrifugation at 100,000×g during 30 min at 4° C. and used either immediately or stored at −20° C.

12. Phosphoinositides determination. Cells expressing the rNTR1 or NTR2 were grown in 12-well plates for 15–18 hr in the presence of 1 $\mu$Ci of myo-[ 3H]inositol (ICN) in a serum-free HAM's-F-10 medium. Cells were washed with Earle buffer, pH 7.5, (25 mM Hepes, 25 mM Tris, 140 mM NaCl, 5 mM KCl, 1.8 mM CaCl$_2$, 0.8 mM MgCl$_2$, 5 mM glucose) containing 0.1% bovine serum albumin, and incubated for 15 min at 37° C. in 900 $\mu$l of 30 mM LiCl in Earle buffer. Neurotensin$_{1-13}$ was then added at the indicated concentrations for 15 min. The reaction was stopped by 750 $\mu$L of ice cold 10 mM HCOOH, pH 5.5. After 30 min at 4° C., the supernatant was collected and neutralized by 2.5 mL of 5 mM NH$_4$OH. Total [$^3$H]phosphoinositides (PIs) were separated from free [$^3$H]inositol on Dowex AG-X8 (Bio-Rad) (Van Renterghem et al., 1988) chromatography by eluting successively with 5 mL of water and 4 mL of 40 mM and 1 M ammonium formate, pH 5.5. The radioactivity contained in the 1 M fraction was counted after addition of 5 mL of Ecolume (ICN).

13. Identification of a cDNA clone encoding contulakin-G. Contulakin-G encoding clones were selected from a size-fractionated cDNA library constructed using mRNA obtained from a *Conus geographus* venom duct as previously described (Colledge et al., 1992). The library was screened using a specific probe corresponding to amino acids #10–15 of the peptide (5'-ATR ATN GGY TTY TTN GT-3'; SEQ ID NO:3). The oligonucleotide was end-labeled, hybridized and a secondary screening by polymerase chain reaction was performed on 10 clones that hybridized to this probe as previously described (Jimenez et al., 1996). Clones identified in the secondary screen were prepared for DNA sequencing as previously described (Monje et al., 1993). The nucleic acid sequence was determined according to the standard protocol for Sequenase version 2.0 DNA sequencing kit as previously described (Jimenez et al., 1996).

Example 2

Purification of Contulakin-G

Figure 5:
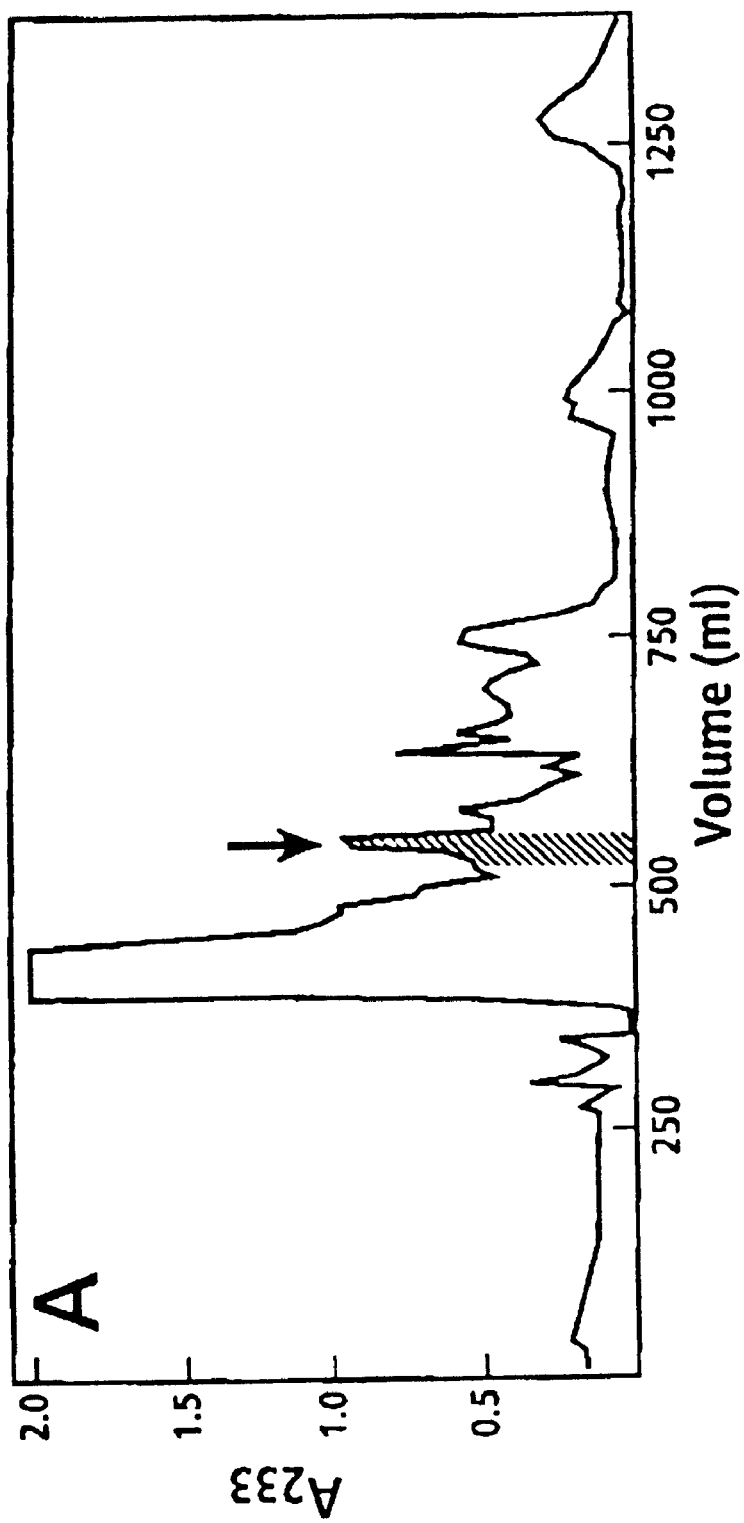

A fraction of *Conus geographus* venom was detected which made mice exceedingly sluggish. Normally, when mice that are sitting down are poked with a rod, they immediately get up and run a considerable distance. Upon i.c.v. injection of the fraction from *Conus geographus* indicated in FIG. 5, the mice had to be poked with much more force before they got up at all, and after getting up, they would walk one or two steps and immediately sit down again. This "sluggish behavior" was followed through several steps of purification, and the apparently homogeneous peptide was further analyzed. This peptide was designated contulakin-G (the Filipino word tulakin' means "has to be pushed or prodded," from the root word tulak, to push). The "G" indicates that the peptide is from *Conus geographus*.

Example 3

Biochemical Characterization of the Purified Contulakin-G

Attempted amino acid sequence analysis of the purified peptide revealed that the peptide was blocked at the N-termninus. Since most N-terminally blocked Conus peptides have a pyroglutamate residue at position 1, the peptide was treated with pyroglutamate aminopeptidase. This resulted in a shift in retention time suggesting removal of a pyroglutamate residue. After enzyme treatment, the sequence Ser-Glu-Glu-Gly-Gly-Ser-Asn-Ala-Xaa-Lys-Lys-Pro-Tyr-Ile-Leu (SEQ ID NO:4) was obtained by standard Edman methods confirming removal of the pyroglutamate residue, where Xaa indicates no amino acid was assigned in the 9th cycle (at position 10) although a very low signal for threonine was obtained. Amino acid analyses were consistent with the presence of one threonine residue in the peptide.

In order to confirm the nature of the amino acid residue in position 10, a cDNA clone encoding the peptide was isolated. The nucleotide sequence and presumed amino acid sequence revealed by the clone are shown in Table 1 and in SEQ ID NO:5 and SEQ ID NO:6, respectively. The amino acid sequence of contulakin-G obtained by direct Edman sequencing is found encoded towards the C-terminal end of the only significant open reading frame in the clone (at residues 51–66); the predicted amino acid sequence reveals that position 10 of the mature peptide (residue 60 of the precursor) is encoded by a codon for threonine. Thus, the Edman sequencing, together with cloning results, suggested that a modified threonine residue was present in position 10.

TABLE 1

Figure 6:
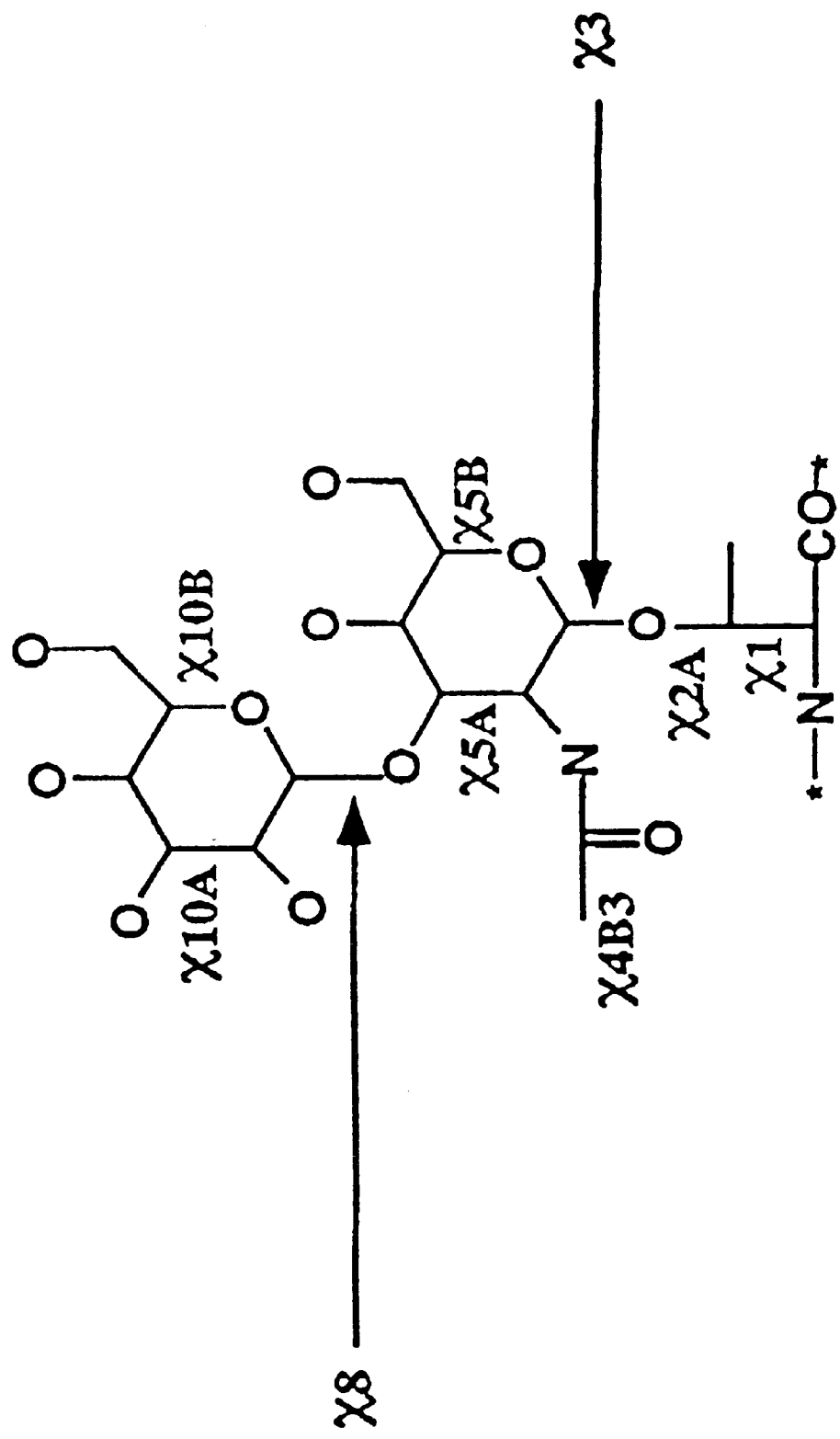

DNA (SEQ ID NO:5) and Peptide (SEQ ID NO:6) Sequences of Contulakin-G atg cag acg gcc tac tgg gtg atg gtg atg atg atg gtg tgg att gca
Met Gln Thr Ala Tyr Trp Val Met Val Met Net Met Val Trp Ile Ala gcc cct ctg tct gaa ggt ggt aaa ctg aac gat gta att cgg ggt ttg
Ala Pro Leu Ser Glu Gly Gly Lys Leu Asn Asp Val Ile Arg Gly Leu gtg cca gac gac ata acc cca cag ctc atg ttg gga agt ctg att tcc
Val Pro Asp Asp Ile Thr Pro Gln Leu Met Leu Gly Ser Leu Ile Ser cgt cgt caa tcg gaa gag ggt ggt tca aat gca acc aag aaa ccc tat
Arg Arg Gln Ser Glu Glu Gly Gly Ser Asn Ala Thr Lys Lys Pro Tyr att cta agg gcc agc gac cag gtt gca tct ggg cca tag
Ile Leu Arg Ala Ser Asp Gln Val Ala Ser Gly Pro Mass spectrometric analyses (MALD, LSI and nano-ESI) of the purified contulakin-G fraction revealed a variety of intact species as summarized in Table 2. Some variation in the intensity of the different species was observed with different ionization techniques, which was ascribed to differences in the bias (Craig et al., 1994) with each ionization technique. In the following analysis, we have concentrated on the major glycoform with intact mass $M_1=2069$ observed with all of the ionization techniques investigated. The difference between the observed mass (2069 Da) and the mass calculated for the sequence assuming Thr at residue 10 (1703.83 Da) was 365 Da. Because one possible modification of threonine is O-glycosylation, we proposed, based on this mass difference, that the unidentified residue was hexose-N-acetyl-hexosamine-threonine (Hex-HexNAc-Thr) which would result in the addition of 365.13 Da. The observed masses (Table 2) are consistent with the calculated monoisotopic mass of the $[M_1+H]^+$ or $[M_1+2H]^{2+}$ of the proposed disaccharide-linked peptide (2069.98 or 1035.5 Da respectively). Intense fragment ions were observed in the nano-ESI MS/MS mass spectrum of the doubly charged $[M_1+2H]^{2+}$ intact molecule ion of contulakin-G (FIG. 6) corresponding to the loss of the complete Hex-HexNAc glycan (denoted $P(\chi_3)_{10}$ (Craig et al., 1993) or loss of the terminal hexose residue $(P(\chi_8)_{10})$.

TABLE 2

Species Observed with MALD, LSI and nano-ESI Analysis of Purified Contulakin-G

| Molecule Species | $M_1$ (Da) | $M_2$ (Da) | $M_3$ (Da) | $M_4$ (Da) |
|---|---|---|---|---|
| Proposed glycan | HexHexNAc | SO$_4$HexHexNAc | Hex$_3$ | Hex$_2$HexNAc$_2$ |
| MALD/TOF | 2069[a] | — | 2186[b] | — |
| LSI/Magnetic | 2068.7 | 2149.6 | — | 2436.5 |
| nano-ESI/IT | 2068.6[c] | 2148.6[c] | — | — |
| Mono[d] [M + H]$^+$ | 2068.97 | 2148.92 | 2189.94 | 2434.10 |
| Average[e] [M + H]$^+$ | 2070.19 | 2150.25 | 2191.27 | 2435.53 |

[a] m/z 2091 and 2107 corresponding with [M$_1$ + Na]$^+$ and [M$_1$ + K]$^+$ were also observed.
[b] m/z 2210 and 2225 corresponding with [M$_3$ + Na]$^+$ and [M$_3$ + K]$^+$ were also observed.
[c] m/z 1035.3 and 1075.3 doubly charged ions were observed.
[d] monoisotopic [M + H]$^+$ masses were calculated based on proposed glycan and contulakin-G sequence.
[e] average [M + H]$^+$ masses were calculated based on proposed glycan and contulakin-G sequence.

Example 4

Evidence that Thr-10 is O-glycosylated

Native contulakin-G was treated with β-galactosidase isolated from bovine testes. This enzyme preferentially hydrolyzes terminal β1→3 galactopyranosyl residues from the non-reducing end of glycoconjugates. After β-galactosidase treatment of the native sample a new component was observed on RP-HPLC. This component was collected and analyzed with MALD-MS in which a species was observed at m/z 1907. The difference in mass and the specificity of the enzyme are consistent with a terminal galactose residue being released. Based on the β-galactosidase hydrolysis results we reasoned that the glycan moiety might be susceptible to O-glycosidase treatment, which liberates the disaccharide Gal (β1→3) GalNAc (α1→) bound to serine or threonine as a core unit of glycopeptides. O-glycosidase treatment of the native contulakin-G did in fact result in a new species after the enzyme hydrolysis mixture was analyzed on RP-HPLC. The new component was collected and analyzed with MALD-MS where an m/z 1704 species was observed consistent with loss of Hex-HexNAc (i.e., the mass was consistent with that predicted for the peptide with an unmodified threonine residue at position 10). The enzyme hydrolysis results are consistent with the presence of a Gal (β1→3) GalNAc (α1→) glycan. Based on the O-glycosidase and the β-galactosidase hydrolysis results, the structure of the most abundant glycopeptide is:

Example 5

Synthesis of the Non-Glycosylated and Glycosylated Contulakin-G

The 16-amino acid non-glycosylated peptide was chemically synthesized. The synthetic material was found to have the same retention time as the enzymatically des-glycosylated contulakin-G on RP-HPLC. The 16-amino acid glycosylated contulakin-G containing Gal (β-1→3) GalNAc (α1→) attached to Thr$_{10}$ was also synthesized. This synthetic glycosylated contulakin-G co-eluted with the native contulakin-G on RP-HPLC. The post source decay fragmentation spectra observed for both native and synthetic contulakin-G showed very similar fragmentation patterns.

Example 6

Biological Potency of Synthetic Glycosylated and Non-Glycosylated Contulakin-G

The loss of motor control for which the native contulakin-G was originally isolated, together with gut contraction, absence of preening/grooming, and reduced sensitivity to tail depression were signs observed when Neurotensin$_{1-13}$, non-glycosylated Thr$_{10}$-contulakin-G or synthetic contulakin-G were administered icv. In order to investigate these observations in more detail, a dose response comparison was performed as detailed in Table 3. While the non-glycosylated Thr$_{10}$-contulakin-G analog was active at doses of 1 nmol and higher, it was inactive at 300 pmol doses. In contrast, contulakin-G was found to elicit loss of motor control at doses of 30 pmol or approximately 5 pmol/g.

TABLE 3

Effect of icv administration of Neurotensin$_{1-13}$, Thr$_{10}$-Contulakin-G and Contulakin-G in 14–18 day old mice

| Compound | dose (pmol) | Number of mice[a] | Av. age (days) | weight (g)[b] | A[c] (min) | B[c] (min) | R[c] (min) |
|---|---|---|---|---|---|---|---|
| NSS | 0 | 8 | 16 | 6.2 | —[d] | —[d] | —[d] |
| neurotensin$_{1-13}$ | 1000 | 2 | 14 | 7.1 | 9 | 23 | >120 |
| Thr$_{10}$-contulakin-G | 1000 | 7 | 16.6 | 6.5 | 9 | 99 | 159 |
| Thr$_{10}$-contulakin-G | 300 | 6 | 15.7 | 6.1 | —[d] | —[d] | —[d] |
| contulakin-G | 1000 | 6 | 18 | 7.1 | 1.0 | 120 | 187 |
| contulakin-G | 300 | 8 | 15.5 | 6.6 | 2.9 | 42 | 151 |

```
              Gal (β1->3) GalNAc (α1->)                (SEQ ID NO:_)
                                    |
pGlu-Ser-Glu-Glu-Gly-Gly-Ser-Asn-Ala-Thr-Lys-Lys-Pro-Tyr-Ile-Leu-OH
```

TABLE 3-continued

Effect of icv administration of Neurotensin$_{1-13}$, Thr$_{10}$-Contulakin-G and Contulakin-G in 14–18 day old mice

| Compound | dose (pmol) | Number of mice[a] | Av. age (days) | weight (g)[b] | Time of symptom | | |
|---|---|---|---|---|---|---|---|
| | | | | | A[c] (min) | B[c] (min) | R[c] (min) |
| contulakin-G | 100 | 8 | 15.9 | 6.6 | 2.8 | 40 | 136 |
| contulakin-G | 30 | 7/9 | 15 | 6.3 | 5.3 | 23 | 114 |

[a]number of mice affected.
[b]average age (days) and weight (g).
[c]average time after which specific behavior observed (observations were made every 2 min for first 15 min and every 15 min thereafter). Symptoms A and B were observed when a mouse was placed onto a bench top after lifting it by the tail for a second. Symptom A: The mouse moved at most a few steps and rested with the hind legs spread out. Mouse remained stationary unless pushed or lifted. Symptom B: The mouse remained sluggish but the position of the hind part of the body when at rest resembled that of the NSS controls. Symptom R: Recovery, the mouse moved freely when released.
[d]no symptom observed.

The six C-terminal amino acids of contulakin-G show significant similarity to the sequences of neurotensin$_{1-13}$, neuromedin, xenin and the C-terminus of xenopsin (see Table 4). Because of the similar signs observed when either contulakin-G or Neurotensin$_{1-13}$ were administered icv and the significant homology between contulakin-G and Neurotensini$_{1-13}$, we tested the affinity of contulakin-G for a number of the cloned neurotensin receptors. As shown in Table 5, the non-glycosylated Thr$_{10}$-contulakin-G analog was found to bind the human neurotensin type 1 receptor (hNTR1) with 10 fold lower affinity than Neurotensin$_{1-13}$, and even lower affinities for the other NTR's. Contulakin-G exhibited significantly lower affinity than the non-glycosylated Thr$_{10}$-contulakin-G analog for all of the NTR's tested.

Both contulakin-G and the non-glycosylated Thr$_{10}$-contulakin-G analog acted as agonists when tested on CHO cells expressing the rNTR1. No response was observed with CHO cells expressing the rNTR2. The non-glycosylated Thr$_{10}$-contulakin-G analog resulted in slightly lower potency (0.6 nM) but with similar efficacy as compared with Neurotensin$_{13}$. The synthetic glycosylated contulakin-G potency was significantly lower (20–30 nM) and the agonistic efficacy was approximately half that observed for Neurotensin$_{1-13}$.

References (1) Carraway et al., 1973; (2) Minamino et al., 1984;
(3) Araki et al., 1973; (4) Feurle et al., 1992.

TABLE 5

Comparison of Binding Affinity of Neurotensin$_{1-13}$, Thr$_{10}$-Contulakin-G and Contulakin-G for the Cloned Human and Rat Neurotensin Type 1 Receptor (NTR1), the Rat Neurotensin Type 2 Receptor (rNTR2), and the Solubilized Mouse Neurotensin Type 3 Receptor (mNTR3)

| Compound | IC$_{50}$ (nM) Receptor | | | |
|---|---|---|---|---|
| | hNTR1 | rNTR1 | rNTR2 | mNTR3 |
| neurotensin$_{1-13}$ | 1.4 | 3.2 | 6.0 | 1.4 |
| Thr$_{10}$-contulakin-G | 23 | 79 | 170 | 71 |
| contulakin-G | 960 | 524 | 730 | 250 |

Example 7

Biological Activity of Contulakin-G Analogs

The biological activity of several peptide analogs of contulakin-G was tested in a similar manner as described above by icv injection in mice. These peptides were synthesized as described herein, and include the following analogs:

Ser$_{10}$-contulakin-G containing the native glycosylation on Ser$_{10}$ (analog A); and Δ1-9-Ser$_{10}$-contulakin-G containing the native glycosylation on Ser$_{10}$ (analog B)

It was found that analog A was slightly more active than the native contulakin-G. It was also found that analog B had the same activity, i.e., onset and recovery time than analog A when tested in two week old mice at a dose of 100 pmole. In this test, the mice were still not able to right themselves after 75 minutes. When tested in three week old mice at doses of 1 nmole and 300 pmole, the same activity was seen between the analogs and these mice were drowsy for 100 minutes. These experiments demonstrate that glycosylated contulakin-G analogs in which N-terminal amino acids residues have been removed, retain activity. Similar results are achieved for other analogs, such as Δ1-5-Ser$_6$-contulakin-G containing the native glycosylation on Ser$_6$ with or without the native glycosylation on Thr$_{10}$. These results show that the placement of a glycosylated serine residue proximal to the site of truncation yields active analogs.

TABLE 4

Sequence Comparison of Contulakin-G and Members of the Neurotensin Family of Peptides

| Name | Sequence (SEQ ID NO:) | Id[a] | Si[b] | Source | Ref |
|---|---|---|---|---|---|
| Contulakin-G | <ESEEGGSNAT*KKPYIL-OH (7) | — | — | C. geographus | |
| neurotensin | <ELYENKPRRPYIL-OH (8) | 66 | 33 | bovine hypothalamus | (1) |
| neuromedin N | KIPYIL-OH (9) | 83 | 0 | porcine spinal cord | (2) |
| xenopsin | QGKRPWIL-OH (10) | 66 | 16 | Xenopus laevis | (3) |
| xenin | MLTKFETKSARVKGLSFHPKRPWIL-OH (12) | 66 | 16 | human gastric mucosa | (4) |

*indicates an O-linked glycosylated threonine/serine residue.
[a]percentage identity of the 6 C-terminal amino acids compared to contulakin-G$_{11-16}$.
[b]percentage similarity of the 6 C-terminal amino acids compared to contulakin-G$_{11-16}$.

The Conus peptide characterized above, contulakin-G, has a novel biochemical feature: a post-translationally O-glycosylated threonine not previously found in Conus peptides. Using mass spectrometry and specific enzymatic hydrolyses, it was found that $Thr_{10}$ was modified with the disaccharide Gal ($\beta1 \rightarrow 3$) GalNAc ($\alpha1 \rightarrow$). The corresponding glycosylated and non-glycosylated forms of contulakin-G were synthesized which confirmed the molecular structure of this major glycosylated form of the native molecule based on RP-HPLC co-elution and MS fragmentation criteria. The masses of the other more minor molecule species observed with mass spectrometry are consistent with glycan structural variations at peripheral sites on the characterized oligosaccharide core unit (Baenziger, 1994).

An analysis of a cDNA clone encoding contulakin-G reveals that the prepropeptide organization of the contulakin-G precursor is similar to that of other Conus peptide precursors (Olivera et al., 1997). A typical signal sequence is found, and immediately N-terminal to the contulakin-G sequence are two basic amino acids which presumably signal a proteolytic cleavage to generate the N-terminus of the mature peptide (the glutamine residue would cyclize to pyroglutamate either spontaneously or due to the action of glutaminyl cyclase (Fischer et al., 1987)). Although in most respects the contulakin-G precursor has the same organization as all other Conus venom peptide precursors and would be predicted to be processed in the same way, the ten C-terminal amino acids predicted by the clone are not present in contulakin-G purified from venom. One possibility is that the clone represents a different variant, for example one which was alternatively spliced. Alternatively, further proteolytic processing at the C-terminus may be required to generate mature contulakin-G.

Over the last 20 years an increasing number of biologically important glycopeptides and glycoproteins have been identified. Vespulakinin 1, first identified by Pisano et al. (Yoshida et al., 1976), is, to our knowledge, the only other O-glycosylated peptide toxin which has been isolated from venom other than Conus. Vespulakinin 1 was extracted from the venom sacs of the yellow jacket wasp, *Vespula maculitrons*. The peptide (TAT*T*RRRGRPPGFSPFR-OH (SEQ ID NO:12) where the asterisk indicates an O-linked glycosylated threonine residue) contains two sequential sites of O-linked glycosylation. The C-terminus of Vespulakinin is identical to the sequence of Bradykinin (RPPGFSPFR-OH (SEQ ID NO:13)) and the peptide was found to elicit a number of signs also elicited by Bradykinin. Vespulakinin is therefore another example of an O-linked glycosylated peptide toxin in which the C-terminus appears to target a mammalian neurotransmitter receptor. Thus, both contulakin-G and Vespulakinin I contain glycosylated N-terminal extensions to sequences with very high homology to mammalian neuropeptides. κA-conotoxin SIVA, a $K^+$ channel inhibitor is unusual among disulfide-rich Conus peptides in having a long N-terminal tail, which has an O-glycosylated residue (Craig et al., 1998).

For most Conus peptides, a specific conformation appears to be stabilized either by multiple disulfide linkages or by the appropriate spacing of γ-carboxyglutamate residues to promote formation of α-helices (Olivera et al., 1990). Conus peptides without multiple disulfides comprise a most eclectic set of families, including the conopressins, conantokins, contryphans and now contulakin-G. The conopressins are probably endogenous molluscan peptides, clearly homologous to the vassopressin/oxytocin family of peptides; these are more widely distributed in molluscan tissues than in Conus venom ducts. However, the other non-disulfide-rich peptides (conantokins, contryphans and contulakin-G) may be specialized venom peptides exhibiting unusual post-translational modifications. In addition to the O-glycosylated threonine moiety of contulakin-G described here, γ-carboxylation of glutamate residues and the post-translational epimerization and bromination of tryptophan residues were discovered in conantokins and contryphans.

Several lines of evidence are consistent with contulakin-G being the first member of the neurotensin family of peptides to be isolated from an invertebrate source. First, the C-terminal region of contulakin-G exhibits a striking degree of similarity to other members of the neurotensin family (all from vertebrates), as shown in Table 4. Furthermore, it was shown above that contulakin-G competes for binding to three known neurotensin receptor subtypes; evidence that contulakin-G acts as an agonist on a cloned neurotensin receptor is also presented above. Most convincingly however, when contulakin-G is injected into mice, the same behavioral signs are elicited with administration of neurotensin. Thus, structural data, binding data and in vivo behavioral symptomatology are all consistent with the assignment of contulakin-G to the neurotensin family of peptides.

Clearly, both contulakin-G and the non-glycosylated $Thr_{10}$-contulakin-G are rNTR1agonists at physiologically relevant concentrations (20–30 and 0.6 nM, respectively). The observed agonistic effects of both contulakin-G and the non-glycosylated analog, as well as the absence of any agonistic effect of these ligands on CHO cells expressing rNTR2 using the IP accumulation assay does not correlate with the in vitro binding data; both peptides are agonists at concentrations significantly below their $IC_{50}$ binding affinity (524 and 79 nM, respectively). Most unexpected therefore, given its apparently lower binding affinity, is the increased potency of glycosylated contulakin-G compared with the non-glycosylated analog after icv administration.

Thus, the role of the glycan is somewhat paradoxical. In vitro, the glycan neither increases the binding affinity, the agonistic potency nor agonistic efficacy. In contrast, in vivo, the glycan significantly increases the potency of the peptide. One simple explanation is that the increased potency of contulakin-G compared with the non-glycosylated analog is due to increased stability. An alternative mechanism for the increased potency is transport to the site of action facilitated by the glycan. Additionally, the glycosylated peptide may act with high affinity on an as-yet-undefined neurotensin receptor subtype (Tyler et al., 1998), or may be a selective high affinity ligand for a particular state of a neurotensin receptor subtype. Yet another possibility is that the relevant targeted neurotensin receptors may be closely co-localized with carbohydrate binding sites, and that the glycan may serve as an "address label", a mechanism postulated for certain opiate peptides. Preliminary data supporting the increased stability hypothesis has been obtained— proteolytic degradation of contulakin-G is inhibited by the presence of the glycan moiety. The increased stability may well result in an enhanced supply of the glycopeptide at the receptor. However, the increased in vivo potency of contulakin-G conferred by O-glycosylation clearly requires a more balanced evaluation of the possibilities outlined above.

Example 8

Materials and Methods for Assessing Analgesic Activity of $Thr_{10}$-Contulakin-G 1. Acute pain (hotplate). $Th_{10}$-contulakin-G (CGX-1063) or vehicle was administered via intracerebroventricular (icv)

in a volume of 5 μl. Fifteen minutes after injection, animals were placed on a 55° C. hotplate. The latency to the first response (flinch), a spinally mediated behavioral response, and the first hindlimb lick, a centrally organized motor response to acute pain, were recorded. Mice were removed from the hotplate after 60 seconds if no response was observed. Immediately prior to being placed on the hotplate, motor function was tested by determining the latency to first fall from an accelerating rotarod.

2. Persistent pain (formalin test). Intrathecal (it) drug injections were performed as described by Hyldon and Wilcox (1980). CGX-1063 (10 or 100 pmol) or vehicle was administered in a volume of 5 μl. Fifteen minutes after the it injection, the right hindpaw was injected with 20 μl of 5% formalin. Animals were placed in clear plexiglass cylinders backed by mirrors to facilitate observation. Animals were closely observed for 2 minutes per 5 minute period, and the amount of time the animal spent licking the injected paw was recorded in this manner for a total of 45–50 minutes. Results are expressed as licking time in seconds per five minutes. At the end of the experiment, all animals were placed on an accelerating rotorod and the latency to first fall was recorded.

2. Neuropathic pain. The partial sciatic nerve ligation model was used to assess the efficacy of CGX-1063 in neuropathic pain. Nerve injury was produced according to the methods of Malmberg and Basbaum (1998). Animals were anesthetized with a ketamine/xylazine solution, the sciatic nerve was exposed and tightly ligated with 8-0 silk suture around ⅓ to ½ of the nerve. In sham-operated mice the nerve was exposed, but not ligated. Animals were allowed to recover for at least 1 week before testing was performed. On the testing day, mice were placed in plexiglass cylinders on a wire mesh frame and allowed to habituate for at least 60 minutes. Mechanical allodynia was assessed with calibrated von Frey filaments using the up-down method as described by Chaplan et al. (1994), and the 50% withdrawal threshold was calculated. Animals that did not respond to any of the filaments in the series were assigned a maximal value of 3.6 grams, which is the filament that typically lifted the hindlimb without bending, and corresponds to approximately ⅒ the animal's body weight.

Example 9

Analgesic Activity of $Thr_{10}$-Contulakin-G

Figure 7A:
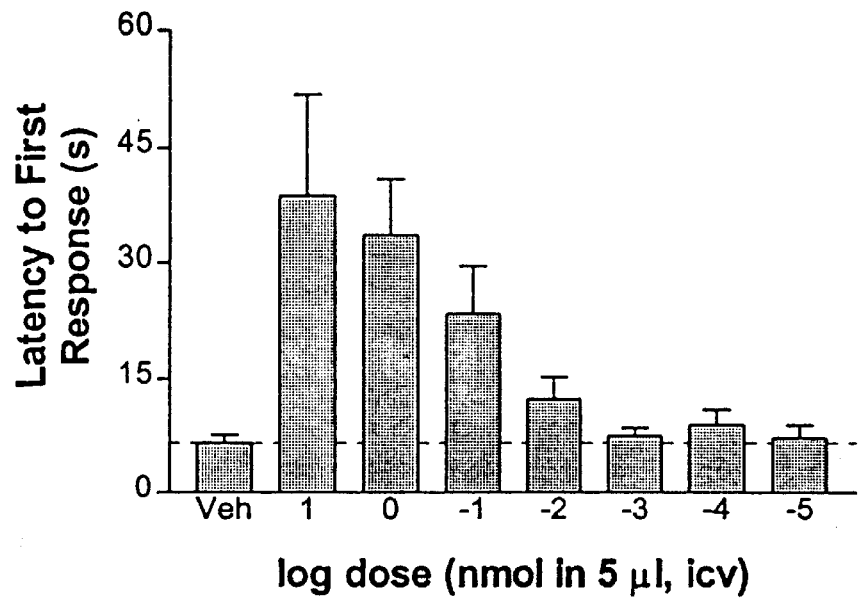
Figure 7B:
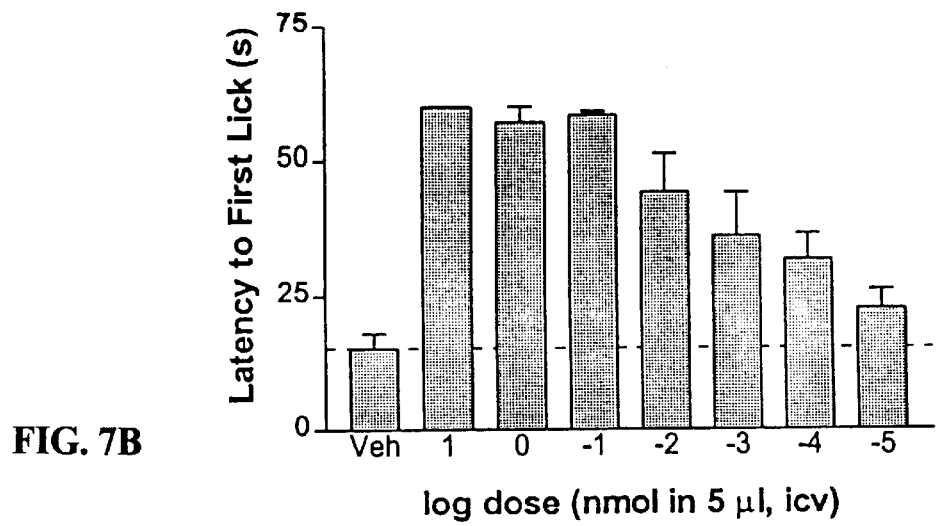
Figure 7C:
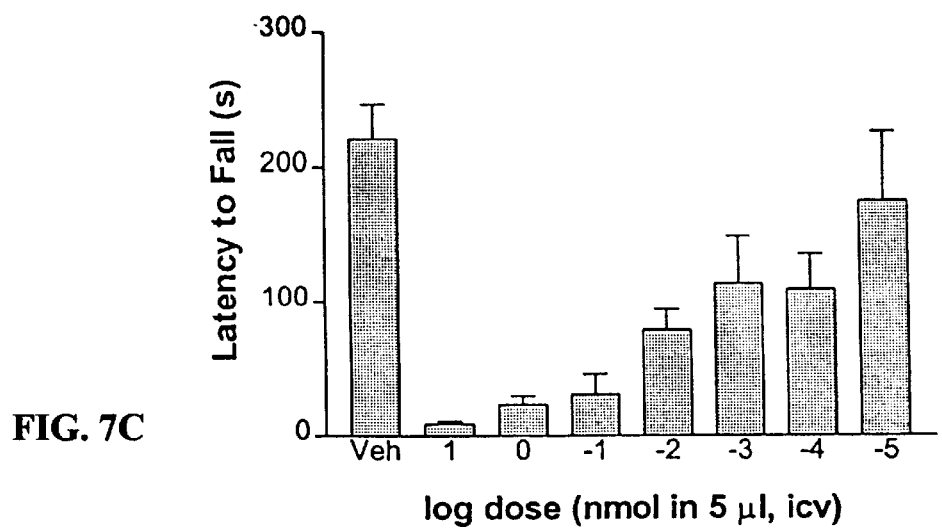

CGX-1063 (10 fmol–10 nmol, icv) dose-dependently increased the latency to the first hindpaw lick and first response elicited by the hotplate (FIGS. 7A–7B). Of interest is the difference in potency of CGX-1063 in increasing the latency to the first hindpaw lick compared to the latency to first response. CGX-1063 also dose-dependently decreased the latency to first fall on the rotarod (FIG. 7C). However, this apparent motor impairment did not appear to be the result of the loss of motor function, since animals were capable of normal locomotor activity when stimulated. Thus, the effect of CGX-1063 on the hotplate unequivocally was an analgesic effect.

Figure 8A:
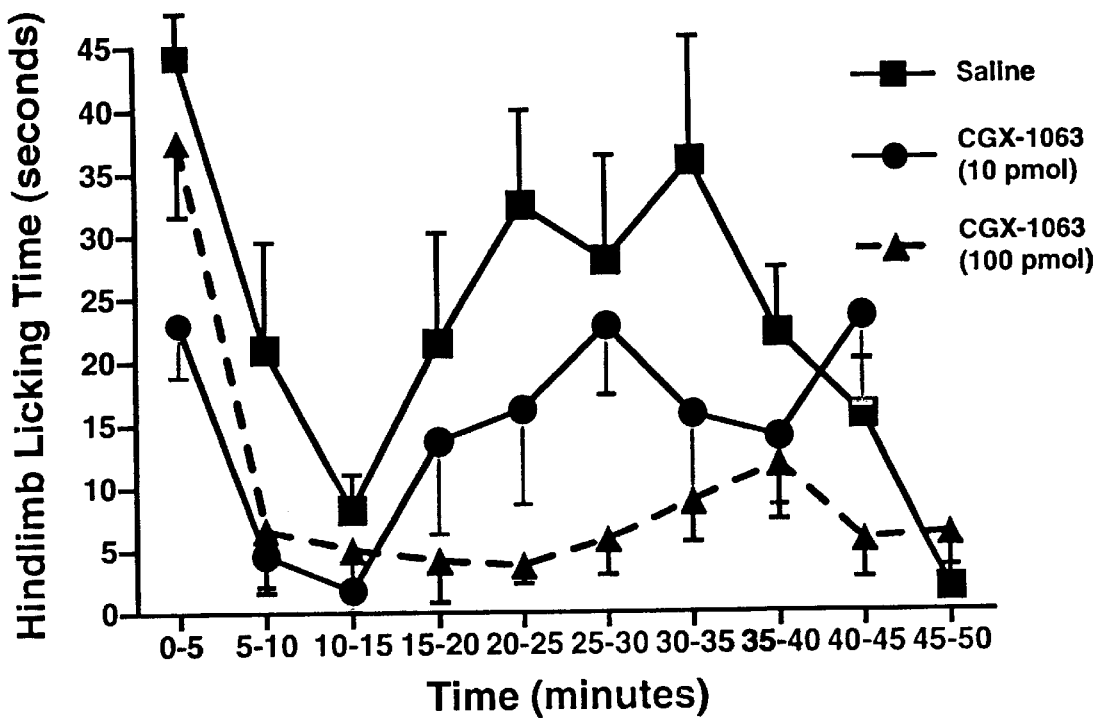
Figure 8B:
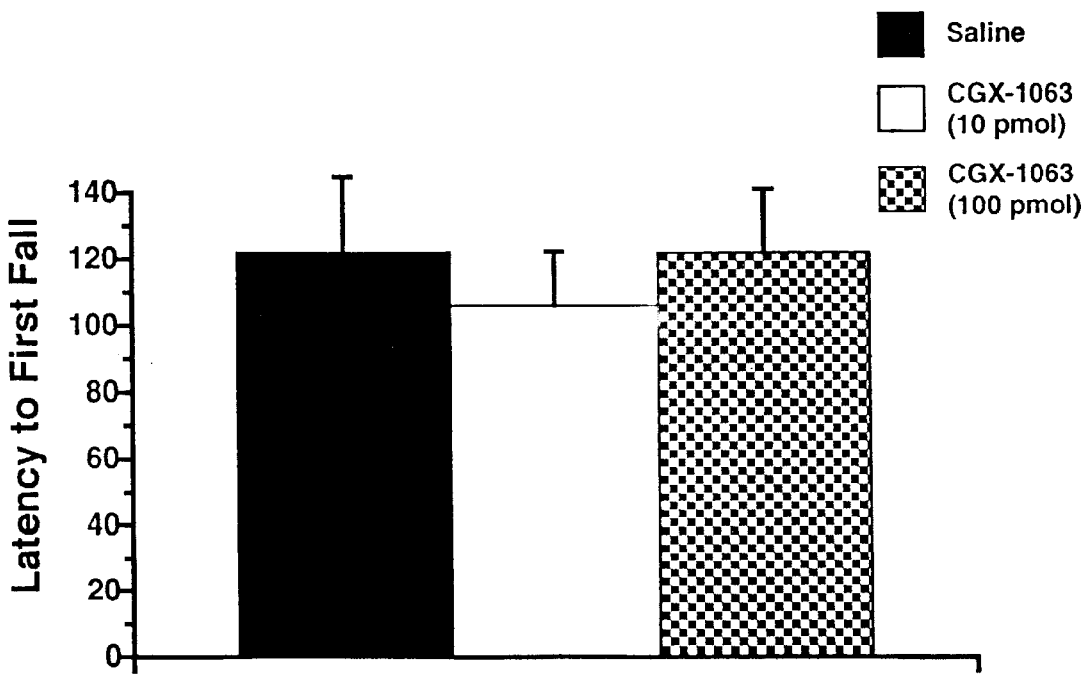

CGX-1063 (10 or 100 pmol, it) dose-dependently and significantly decreased the second phase of the formalin test (FIG. 8A). Interestingly, the lower dose (10 pmol) was more effective in decreasing the first phase response time than was the higher dose. This will be examined in more detail in future experiments. After it administration, CGX-1063 treated animals showed no motor impairment compared to vehicle treated animals (FIG. 8B), indicating that the effect of icv CGX-1063 (observed in the hotplate test above) on motor impairment is mediated at higher brain regions, not spinally, and that the analgesic effects of CGX-1063 can be separated from the motor toxicity by using this route (it) of administration. The downward shift in the rotorod scores compared to those from animals used in the hotplate test reflects an overall impairment in these animals due to formalin-induced allodynia and inflammation of the hindpaw.

Figure 9:
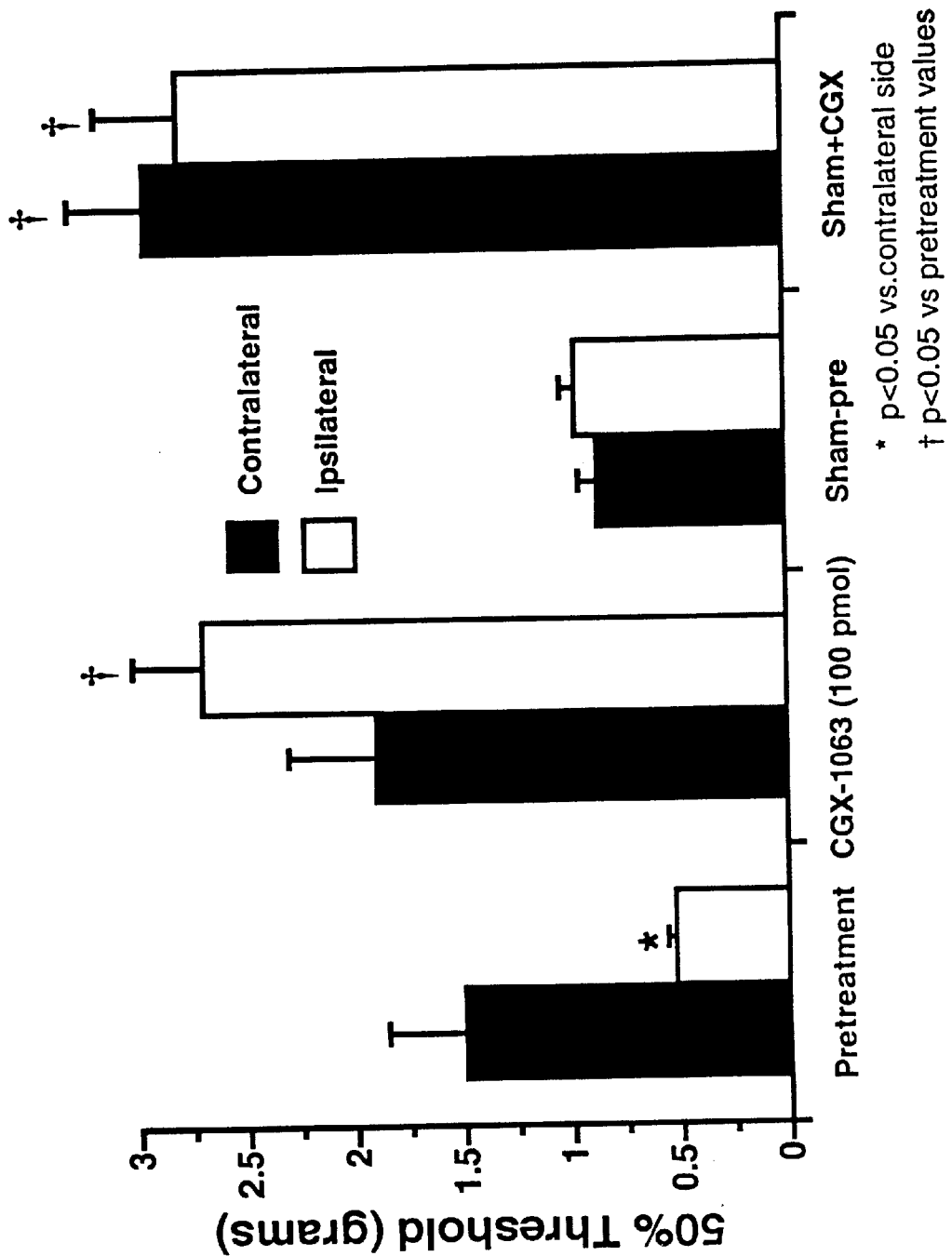

One week after partial sciatic nerve ligation, animals showed a marked decrease in the paw withdrawal threshold on the operated side (ipsilateral) relative to the unoperated side (contralateral), indicating an increase in sensitivity to mechanical stimuli (FIG. 9). Intrathecal administration of CGX-1063 (100 pmol) dramatically increased the withdrawal threshold on the ligated side (an approximate six fold increase). Interestingly, the mechanical threshold on the contralateral side was not significantly altered. In sham-operated animals, there was no difference in withdrawal threshold between operated and un-operated sides. After intrathecal CGX-1063, the withdrawal threshold was uniformly increased in both hindpaws of these animals.

The present data demonstrate that CGX-1063 has potent analgesic properties in three commonly used models of pain: acute, persistent/inflammatory and neuropathic pain models. CGX-1063 administered centrally (icv) dose-dependently reduced the response latency in the hot plate model of acute pain, and was effective in the low picomole to high femtomole range. Preliminary data indicate that the analgesic effect of CGX-1063 in this model is not mediated through an opioid mechanism. CGX-1063 was also effective in reducing nociceptive activity in the formalin model of persistent/inflammatory pain. CGX-1063 dose-dependently reduced the second (inflammatory) phase of the formalin test, while at the lower dose, reduced phase one activity. Finally, CGX-1063 showed profound analgesic activity in a model of neuropathic pain. Mechanical withdrawal thresholds in this model were increased nearly six fold compared to pre-treatment values, while not altering sensitivity in the non-injured paw, possibly indicating that CGX-1063 reduces neuropathic allodynia while not affecting normal sensory transmission.

Example 10

Materials and Methods for Assessing Analgesic Activity of Contulakin-G

1. Acute pain (tail-flick). Drug (contulakin-G (CGX-1160) or $Thr_{10}$-contulakin-G (CGX-1063)) or saline was administered intrathecally (i.t.) according to the method of Hylden and Wilcox (Hylden and Wilcox, 1980) in a constant volume of 5 μl. Mice were gently wrapped in a towel with the tail exposed. At various time-points following the i.t. injection, the tail was dipped in a water bath maintained at 54° C. and the time to a vigorous tail withdrawal was recorded. If there was no withdrawal by 8 seconds, the tail was removed to avoid tissue damage.

2. Persistent pain (formalin test). CGX-1160, CGX-1063 (1, 10 or 100 pmol), neurotensin (NT) (1,10, 100 or 10000 pmol), or vehicle was administered i.t. in a volume of 5 μl. Fifteen minutes after the i.t. injection, the right hindpaw was injected with 20 μl of 5% formalin. Animals were placed in clear plexiglass cylinders backed by mirrors to facilitate observation. Animals were closely observed for two minutes per five minute period, and the amount of time the animal spent licking the injected paw was recorded in this manner for a total of 45–50 minutes. Results are expressed as licking time in seconds per five minutes. At the end of the experiment, all animals were placed on an accelerating rotorod and the latency to first fall was recorded.

3. Chronic inflammatory allodynia (CFA model). Mice were given intraplantar (i.pl.) injections of 20 μl of CFA into the right hindpaw and returned to their home cage. Three days later mice were placed in plexiglass cylinders on a wire mesh frame and allowed to habituate for at least 60 minutes. Mechanical allodynia was assessed with calibrated von Frey filaments using the up-down method as described (Chaplan et al., 1994), and the 50% withdrawal threshold was calculated. Animals that did not respond to any of the filaments in the series were assigned a maximal value of 3.6 grams, which is the filament that typically lifted the hindlimb without bending, and corresponds to approximately 1/10 of the body weight.

4. Toxicity testing. To accurately assess the motor impairing effects of CGX-1160, CGX-1063, and NT, 50 mice were divided into groups receiving i.t. CGX-1160 or CGX-1063 (1, 10, 100, 500 and 1000 pmol), NT (0.1, 1, 10, and 100 nmol), or saline (n=5 per group except for the highest dose of each compound where n=3). Starting at 15 minutes post injection animals were place on an accelerating rotorod and the latency to first fall was recorded. Animals were retested at 30, 60, 120, 240 and 300 minutes (or until the latency to fall had returned to control values). Rectal temperature was also recorded in these animals at the same time points.

Example 11

Analgesic Activity of Contulakin-G

Figure 10A:
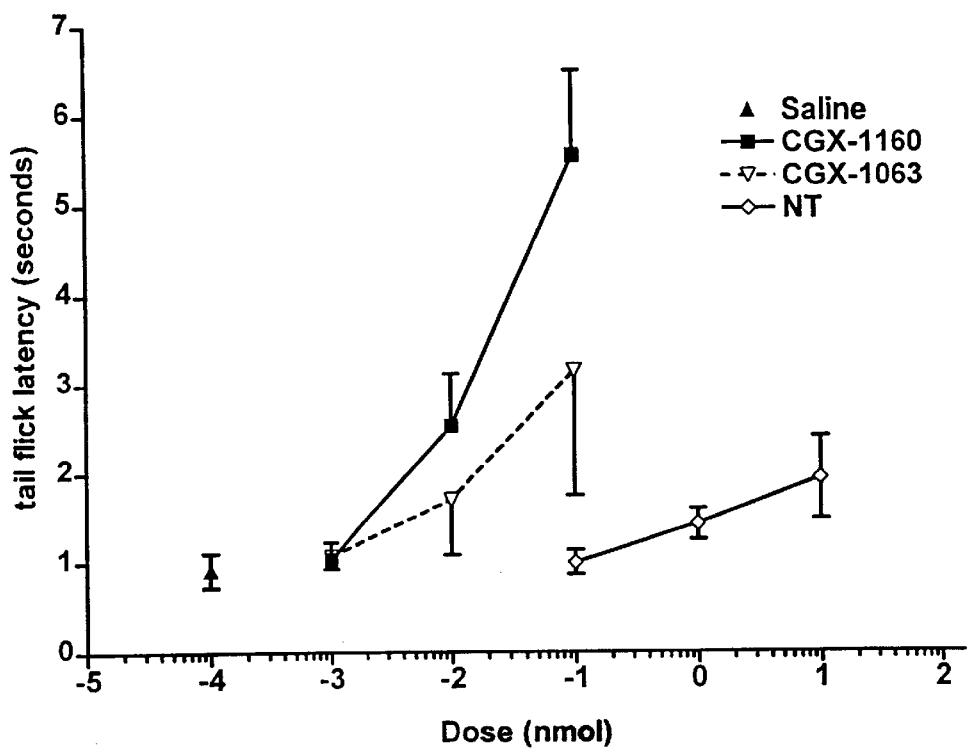
Figure 10B:
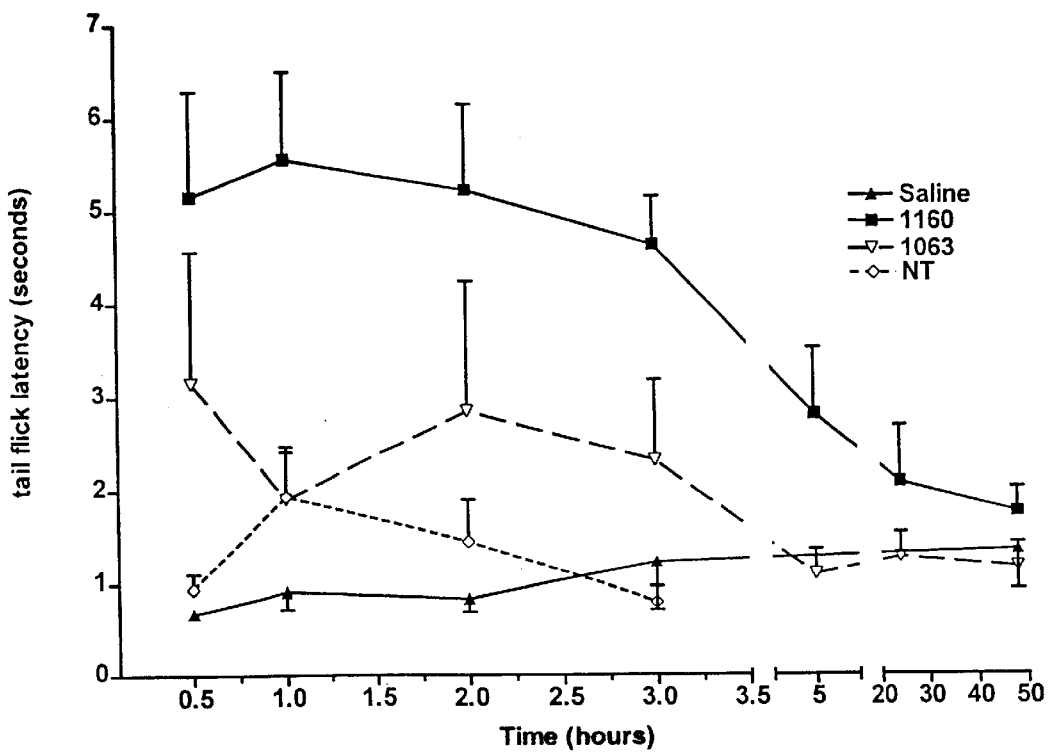

CGX-1160 dose-dependently increased the tail-flick latency (FIG. 10A) with a time to peak effect of ≦30 minutes (the earliest time tested, FIG. 10B). Furthermore, the increase in latency was long-lasting with elevated withdrawal times at 5 hour post injection that returned to baseline at 24 hours post injection (FIG. 10B). CGX-1063 also showed a dose-dependent, though more variable increase in withdrawal latency, and showed only modest antinociceptive efficacy in this model relative to CGX-1160 (FIGS. 10A–10B). In comparison, NT did not significantly elevate withdrawal latency in the tail-flick assay (FIGS. 10A–10B).

Figure 11A:
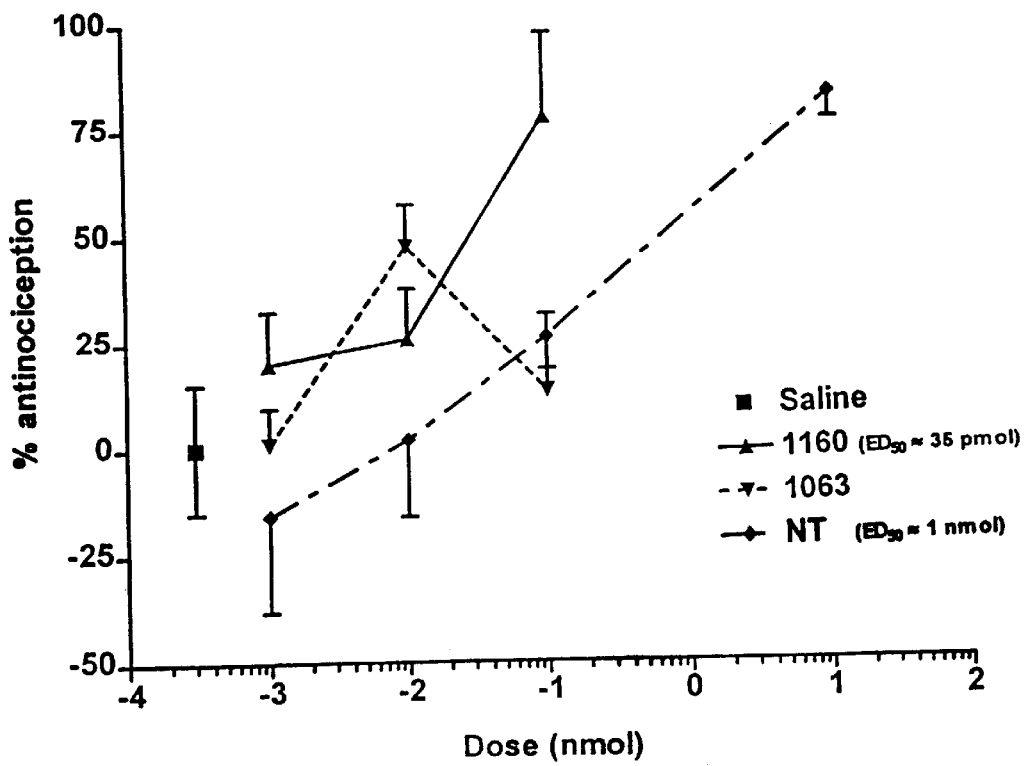
Figure 11B:
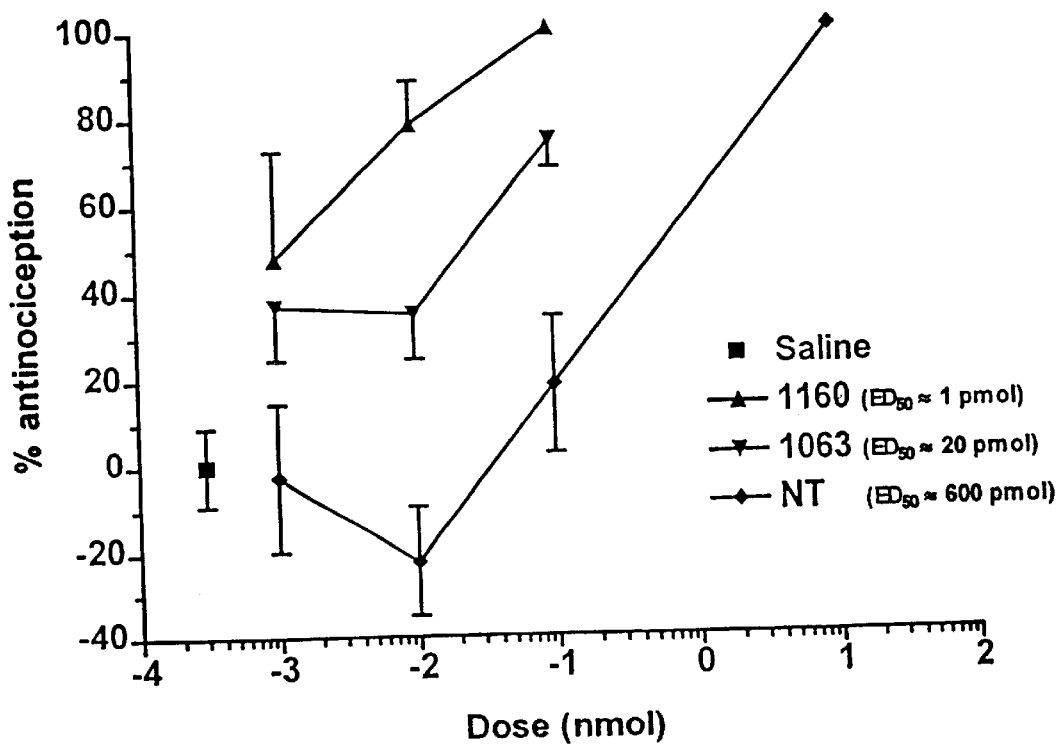

All of the compounds tested dose-dependently showed antinociceptive properties in both phases of the formalin test, but with different potencies. CGX-1160 was the most potent of the three compounds. In phase 1 of the formalin test (FIG. 11A), CGX-1160 had an $ED_{50}$ of approximately 30–40 pmol while NT had an $ED_{50}$ of ≈1 nmol. CGX-1063 did not reach the 50% antinociception threshold in phase 1, however, the irregular dose-response in this test warrants repeating the 100 pmol dose in this assay. In phase 2 of the formalin test, all three compounds dose-dependently reduced the paw licking time (indicated in the figures as an increase in the percent antinociception; FIG. 11B). Again, CGX-1160 was more potent than the other compounds with an estimated $ED_{50}$ of 1 pmol. Lower doses of this compound will be assessed in the future to complete the dose response curve necessary to calculate a more precise $ED_{50}$. CGX-1063 was also effective in reducing nociceptive behavior in phase 2, with an estimated $ED_{50}$ of 10–20 pmol. NT was dramatically less potent than either of the contulakins with an estimated $ED_{50}$ of 600–700 pmol (FIG. 11B).

CGX-1160 showed extremely potent and dose-dependent reversal of CFA-induced mechanical allodynia (FIG. 12A). One-hundred (100) fmol of CGX-1160 given i.t. completely reversed the CFA-induced mechanical allodynia. Interestingly, at this dose, the contralateral sensitivity to mechanical pressure was unaltered indicating a potential unilateral alteration in NT receptors in chronic inflammation. At higher doses of CGX-1160, the mechanical withdrawal threshold in both the CFA-injected paw and the contralateral uninjected paw was dramatically elevated. In FIGS. 12A and 12B, the numbers over the bars indicate the percent increase in mechanical threshold relative to the pre-drug level. As indicated, at all doses tested, CGX-1160 had a much greater antiallodynic effect on the CFA injected side relative to the uninjected side. CGX-1063 was less potent than CGX-1160, but also completely reversed the CFA-induced allodynia (FIG. 12B). The minimally effective dose was 10 pmol, however, at this dose, unlike CGX-1160, the contralateral side was also elevated relative to pre-drug baseline measurements. Consistent with the other models examined in this study, NT showed efficacy in the CFA model at 1 nmol, but not at 100 pmol (FIG. 12C). Other doses of CGX-1160 and NT will be examined in the future to determine accurate $ED_{50}$s for these compounds.

CGX-1160, -1063, and NT all showed dose-dependent effects on locomotor impairment and body temperature. For all three compounds, maximal impairment was at 15 minutes post i.t. injection (locomotor impairment, FIG. 13A) or 30 minutes (hypothermic effects, FIG. 14A). CGX-1063 had no motor toxicity at the lowest dose tested (1 pmol, FIG. 13B), but at higher doses animals showed significant motor toxicity (estimated $TD_{50}$ of 10 pmol, FIGS. 13B and 15A). At 10 pmol this toxicity lasted for 30 minutes, but resolved by 60 minutes. When 100 pmol or 1 nmol was administered, animals were motor impaired for 2–3 hours (FIG. 14A). CGX-1160 was equipotent to CGX-1063 in causing motor impairment (estimated $TD_{50}$ of 10–20 pmol, FIG. 13B). Similar to CGX-1063, at higher doses (100–500× its $ED_{50}$) CGX-1160 showed motor impairment that resolved after 5 hours (FIGS. 13A and 14B). The estimated $TD_{50}$ for NT-induced motor impairment was 3 nmol (FIG. 13B). Similar to the contulakins, at high doses, NT-induced motor impairment that lasted 2–4 hours (FIGS. 13A and 14C).

The hypothermic effects of these compounds were similar to motor toxicity. All three caused a dose-dependent decrease in body temperature. CGX-1160 and -1063 were equipotent with an estimated $TD_{50}$ of 100 pmol (FIG. 15B). However, at this dose CGX-1063 induced a drop in body temperature lasting 2–3 hours (FIGS. 15A and 16A), while the hypothermic effect caused by CGX-1160 resolved by 60 minutes (FIGS. 15A and 16B). At the highest dose of CGX-1160 (500 pmol, 500× the $ED_{50}$), the hypothermic effect had not resolved by six hours post-injection (FIG. 16B). NT showed a very similar dose-response and time course to the contulakins. At the lower doses, NT had no effect or showed a short lasting hypothermic effect (FIG. 16C). At the highest dose, however (100 nmol), NT caused a dramatic and long-lasting hypothermia that had not resolved by three hours (FIGS. 15A and 16C).

The present data show that CGX-1160 and CGX-1063 are potent, broad-spectrum analgesic agents effective in several animal models of acute and chronic pain. CGX-1160 is typically 10 fold more potent than CGX-1063, and 1000 times more potent than NT (Table 6). CGX-1160 is particularly potent in the model of chronic inflammatory pain where CGX-1160 selectively increases the mechanical withdrawal threshold only in the paw receiving the CFA injection, while not altering the threshold of the uninjected paw. This finding indicates that chronic inflammation may lead to a reorganization of NT receptors in nociceptive pathways corresponding to the inflamed paw. Since CGX- 1160 was the only compound in these experiments to show an increased potency, this may indicate an upregulation of a receptor subtype for which CGX-1160 may have particular selectivity and specificity. In support of this hypothesis of CGX-1160 subtype selectivity are the findings that this compound shows antinociception at doses 10–100 fold less than for either locomotor impairment or hypothermia, whereas CGX-1063 and NT cause antinociception, locomotor impairment, and hypothermia at approximately equal doses when administered i.t. Particularly interesting is the long-lasting hypothermic effect of CGX-1063. When given i.t. at 100 pmol (approximately 10 times its $ED_{50}$ in phase 2 of the formalin test, see FIG. 16A), CGX-1063 caused long-lasting hypothermia relative to comparable antinociceptive doses of CGX-1160 (compare the 10 pmol dose in FIG. 16B) and NT (compare the 10 nmol dose in FIG. 16C). This potentially indicates that CGX-1063 is selective for the NT receptor subtype involved in the hypothermic effect of NT analogs. Thus the O-glycosylation of $Thr_{10}$ in CGX-1160 may impart selectivity for the antinociceptive NTR subtype, currently thought to be NTR2, as well as metabolic resistance to peptidases.

TABLE 6

Comparison of the Antinociceptive Effects, Motor Impairment Effects, and Protective Index of CGX-1160, CGX-1063, and NT in the Formalin Test (phase 2) and CFA-Induced Allodynia Test

| Compound | $ED_{50}$, pmol | $TD_{50}$, pmol | PI |
|---|---|---|---|
| Formalin Test (phase 2) | | | |
| CGX-1160 | 1 | 10–20 | 10–20 |
| CGX-1063 | 10–20 | 10–20 | 1–2 |
| NT | 600–700 | 3000 | 5–4.3 |
| CFA-Induced Allodynia Test | | | |
| CGX-1160 | <0.1 | 10–20 | >100 |
| CGX-1063 | <10 | 10–20 | 1–5 |
| NT | ≈500–600 | 3000 | 5–6 |

$ED_{50}$, pmol, estimated from antinociceptive tests
$TD_{50}$, pmol, estimated from rotorod test of minimal motor impairment
Protective Index, PI = $(TD_{50}/ED_{50})$ Example 12

1. Materials and Methods for Assessing Antipsychotic Activity of Contulakin-G 1. Materials. D-amphetamine was obtained from Sigma (St. Louis, Mo.). Contulakin-G (CGX-1160; a synthetic 16 amino acid O-linked glycopeptide) was synthesized as described above.

2. Animals. Male CF-1 mice (30–35g; Charles River Laboratories) were used. All animals were housed in a temperature controlled (23°±3° C.) room with a 12 hour light-dark cycle with free access to food and water. All animals were euthanized in accordance with Public Health Service policies on the humane care of laboratory animals.

3. Locomotor Activity. Animals were placed in clear plastic cages (40 cm×22 cm, 20 cm deep) and allowed to acclimate for 30 minutes. Animals then received either contulakin-G (100 pmol) or saline (vehicle) by freehand intracerebroventricular (i.c.v.) injection (5 μl volume) through a 10 μl Hamilton syringe. After 5 minutes, animals received saline or D-amphetamine sulphate (3 mg/kg) via intraperitoneal (i.p.) administration. Distance traveled (cm) and time spent ambulatory (s) were monitored for 30 minutes using a Videomex-V tracking system (Columbus Instruments, Columbus, Ohio). All testing was done in an isolated, dimly lit behavioral room.

4. Statistics. Data were analyzed using one-way analysis of variance (ANOVA) with drug treatment as the only factor, followed by a Newman-Keuls multiple comparison test for comparison of individual groups, with $P<0.05$ accepted as statistically significant. Statistical analyses were performed with GraphPad PRISM software (Version 2.01, GraphPad, San Diego, Calif.).

Example 13

Antipsychotic Activity of Contulakin-G

A significant effect of drug treatment on locomotor activity as measured by both distance traveled $[F(4,21)=7.87, P<0.05]$ and time spent ambulating $[F(4,21)=6.17, P<0.05]$ was found in the present study. Administration of D-amphetamine resulted in a dose dependent increase in both distance traveled and time spent ambulating (FIGS. 17–18). Pretreatment of mice with contulakin-G (100 pmol i.c.v.) significantly reduced amphetamine-stimulated (3 mg/kg i.p.) increases in distance traveled and time spent ambulating. A reduction in basal locomotor activity (both distance traveled and time spent ambulating) was seen after pretreatment with contulakin-G (100 pmol i.c.v.), however, this reduction did not reach statistical significance.

Converging lines of evidence imply that neurotensin may have antipsychotic properties without the associated adverse side effect profiles of standard neuroleptic drugs (reviewed in (Nemeroffet al., 1992)). Subsequently, many groups have focused on neurotensin analogs as novel antipsychotic drugs. Since contulakin-G shares C-terminal homology with neurotensin, and resembles neurotensin in both in vivo and in vitro assays, the ability of contulakin-G to inhibit D-amphetamine-stimulated locomotor activity, a preclinical screen predictive of antipsychotic efficacy, was assessed. This example demonstrates that pretreatment of mice with contulakin-G significantly reduced amphetamine-stimulated increases in locomotor activity. These data indicate that contulakin-G has similar antipsychotic activity as neurotensin. However as shown above, while neurotensin was far more potent than contulakin-G at the rat neurotensin receptors rNTR1 ($IC_{50}$:3.2 nM for neurotensin; 524 nM for contulakin-G) and rNTR2 ($IC_{50}$:6.0 nM for neurotensin; 730 nM for contulakin-G), and the mouse neurotensin receptor mNTR3 ($IC_{50}$:1.4 nM for neurotensin; 250 nM for contulakin-G), contulakin-G was 1 to 2 orders of magnitude more potent in an in vivo assay (a visually rated assessment of locomotor activity) following i.c.v. administration. These results indicate that contulakin-G and neurotensin may interact with overlapping but distinct populations of neurotensin receptor subtypes or activation states. Thus, contulakin-G would not share the limiting side effects of neurotensin.

Example 14

Materials and Methods for Assessing Anticonvulsant Activity of Contulakin-G

1. Animals. Male Frings (20–25g) were housed in a temperature controlled (23°±1° C.) room with a 12 hour light-dark cycle with free access to food and water. Mice were housed, fed, and handled in a manner consistent with the recommendations in HEW publication (NIH) No. 8623, "Guide for the Care and Use of Laboratory Animals." All mice were euthanized in accordance with Public Health Service policies on the humane care of laboratory animals.

2. Anticonvulsant Assessment. Frings mice were placed in a round, plexiglass jar (diameter 15 cm, height 18 cm) and exposed to a sound stimulus of 110 decibels (11 KHz). Mice were then observed for 25 sec for the presence or absence of hindlimb tonic extension. Animals not displaying hindlimb tonic extension were considered protected.

3. Rotorod Test. Motor impairment was assessed at time of peak effect by placing mice on a rotorod turning at 6 rpm. Animals falling three times in one minute were considered impaired.

Example 15

Anticonvulsant Activity of Contulakin-G

Contulakin-G (CGX-1160) and Thro-contulakin-G (CGX-1063) potently and dose-dependently blocked audiogenic seizures in Frings mice following i.c.v. administration (FIG. 19). Similar to the efficacy in pain models, CGX-1160 was more potent than CGX-1063 with $ED_{50}$s of 7.1 pmol and 27.0 pmol, respectively (Table 7). Also consistent with previous studies, NT was dramatically less potent than CGX-1160 or -1063. Although a dose-response curve for NT has not yet been completed, NT showed 50% protection following 1 nmol administered i.c.v. When tested for motor toxicity, CGX-1160 did not reach the 50% toxic level at doses up to 200 pmol (FIG. 19), whereas the $TD_{50}$ for CGX-1063 is estimated to be approximately 375 pmol resulting in an estimated PI of 14 for the doses tested.

TABLE 7

Anticonvulsant Profile of CGX-1160 and CGX-1063 in Frings AGS Mice Following i.c.v. Administration

| Compound | Time of test (min.)[a] | $TD_{50}$ (pmol) | $ED_{50}$ (pmol) | P.I.[b] | X more potent than NT |
|---|---|---|---|---|---|
| CGX-1160 | 15, 60 | >200 | 7.1 (4.9–8.5) | >28 | ≈140 |
| CGX-1063 | 15, 60 | ≈375 | 27.0 (18.6–34.9) | ≈14 | ≈37 |
| Neurotensin | 15, 60 | not yet determined | ≈1000 | N.D. | |

[a]First time, $TD_{50}$; second time, $ED_{50}$
[b]Protective index = $TD_{50}/ED_{50}$
( ) 95% confidence interval In a separate experiment, the time to peak effect and duration of action of CGX-1160 was examined. I.c.v. administration of 100 pmol (approximately 14X $ED_{50}$) of CGX-1160 showed no activity at 30 minutes, but was 100% protective at 60 minutes, and still showed 50% protection in animals tested 4 hours following i.c.v. injection (FIG. 20).

It will be appreciated that the methods and compositions of the instant invention can be incorporated in the form of a variety of embodiments, only a few of which are disclosed herein. It will be apparent to the artisan that other embodiments exist and do not depart from the spirit of the invention. Thus, embodiments described are illustrative and should not be construed as restrictive.

LIST OF REFERENCES

Annals of Pharmacotherapy 27:912 (1993).
Araki, K. et al. (1973). Chem. Pharm. Bull. (Tokyo) 21:2801–2804.
Barber, M. et al. (1982). Anal. Chem. 54:645A–657A.
Benziger, J. U. (1994). Faseb. J. 8:1019–1025.
Cancer 41:1270 (1993).
Cancer Res. 44:1698 (1984).
Carraway, R. et al. (1973). J. Biol. Chem. 248:6854–6861.
Cartier, G. E. et al. (1996). J. Biol. Chem. 271:7522–7528.
Chabry, J. et al. (1994). J. Neurochem. 63:19–27.
Chaplan, S. R. et al. (1994). J. Neurosci. Methods 53:55–63.
Clineschmidt, B. V. et al. (1979). Eur. J. Pharmacol. 54:129–139.
Colledge, C. J. et al. (1992). Toxicon. 30: 1111–1116.
Cotter, R. J. (1989). Biomed. Mass Spectrom. 18:513–532.
Craig, A. G. et al. (1993). Biol. Mass Spectrom. 22:31–44.
Craig, A. G. et al. (1994). Biol. Mass Spectrom. 23:519–528.
Craig, A. G. et al. (1998). Biochemistry 37:16019–16025.
Cruz, L. J. et al. (1987). Conus geographus toxins that discriminate between neuronal and muscle sodium channels. J. Biol. Chem. 260:9280–9288.
Cusack, B. et al. (1993). J. Recept. Res. 13:123–134.
Cusack, B. et al. (1991). Eur. J Pharmacol. 206:339–342.
Feurle, G. E. et al. (1992). J. Biol. Chem. 267:22305–22309.
Fischer, W. et al. (1987). Proc. Nat. Acad. Sci. USA 84:3628–3632.
Haack, J. A. et al. (1990). Contryphan-T: a gamma-carboxyglutamate containing peptide with N-methyl-d-aspartate antagonist activity. J. Biol. Chem. 265:6025–6029.
Hammerland, L. G. et al. (1992). Eur. J Pharmacol. 226:239–244.
Hillenkamp, F. et al. (1993). Anal. Chem. 63:1193A–1203A.
Horiki, K. et al. (1978). Chemistry Letters 165–68.
Hylden, J. L. K. et al. (1980). Eur. J. Pharmacol. 67:313–316.
Jiménez, E. C. et al. (1996). J. Biol. Chem. 271:28002–28005.
Kaiser et al. (1970). Anal. Biochem. 34:595.
Kapoor (1970). J Pharm. Sci. 59:1–27.
LeNguyen, D. and Rivier, J. (1986). Intl. J. Pep. Prot. 27:285–292.
Luning, B. et al. (1989). Glycoconjugate J. 6:5–19.
Malmberg, A. B et al. (1998). Pain 76:215–222.
Mazella, J. et al. (1988). J. Biol. Chem. 263:144–149.
Mcluckey, S. A. et al. (1991). Anal. Chem. 63:375–383.
Mena, E. E. et al. (1990). Contryphan-G: a novel peptide antagonist to the N-methyl-D-aspartic acid (NMDA) receptor. Neurosci. Lett. 118:241–244.
Methoden der Organischen Chemie (Houben-Weyl): Synthese von Peptiden, E. Wunsch (Ed.), Georg Thieme Verlag, Stuttgart, Ger. (1974).
Minamino, N. et al. (1984). Biochem. Biophys. Res. Commun. 122:542–549.
Monje, V. D. et al. (1993). Neuropharmacology 32:1141–1149.
Munson, P. J. et al. (1980). Anal. Biochem. 107:220–239.
Nishiuchi, Y. et al. (1993). Synthesis of gamma-carboxyglutamic acid-containing peptides by the Boc strategy. Int. J. Pept. Protein Res. 42:533–538.
Nemeroff, C. B. et al. (1992). Ann. N.Y Acad. Sci. 668:146–156.
Norberg, T. et al. (1994). In: Methods in Enzymology, Y. C. Lee Eds., Academic Press, New York, N.Y., pp. 87–107.
Olivera, B. M. et al. (1984). Biochemistry 23:5087–5090.
Olivera, B. M. et al. (1985). Science 230:1338–1343.
Olivera, B. M. et al. (1990). Science 249:257–263.
Olivera, B. M. et al. (1997). Mol. Biol. Cell 8:2101–2109.
Remington's Pharmaceutical Sciences, 18th Ed., Mack Publishing Co., Easton, Pa. (1990).
Rivier, J. R. et al. (1978). Biopolymers 17:1927–38.
Rivier, J. R. et al. (1987). Biochem. 26:8508–8512.
Sadoul, J. L. et al. (1984). Biochem. Biophys. Res. Commun. 120:812–819.
Sambrook, J. et al. (1989). Molecular Cloning: A Laboratory Manual, 2nd Ed., Cold Spring Harbor Laboratory, Cold Spring Harbor, N.Y.

Schroder et al. (1965). *The Peptides* 1:72–75, Academic Press, NY.

Spengler, B. et al. (1992). *Rapid Commun. Mass Spectrom.* 6:105–108.

Stewart, J. M. et al. (1984). In: *Pierce Chemical Company*, Rockford, Ill., pp 176.

Stewart, J. M. et al., *Solid-Phase Peptide Synthesis*, Freeman & Co., San Francisco, Calif. (1969).

Tanaka, K. et al. (1990). *Neuron* 4, 847–854.

Toth, I. et al. (1999). *J. Med Chem.* (JMC ASAP web edition Sept. 22, 1999).

Van Renterghem, C. et al. (1988). *Biochem. Biophys. Res. Comm.* 157:977–985.

Yoshida, H. et al. (1 976). *Biochemistry* 15:61–64.

Zhou L. M., et al. (1996). Synthetic Analogues of Contryphan-G: NMDA Antagonists Acting Through a Novel Polyamine-Coupled Site. *J. Neurochem.* 66:620–628.

U.S. Pat. No. 3,972,859.
U.S. Pat. No. 3,842,067.
U.S. Pat. No. 3,862,925.
U.S. Pat. No. 4,105,603.
U.S. Pat. No. 4,352,883.
U.S. Pat. No. 4,353,888.
U.S. Pat. No. 4,447,356.
U.S. Pat. No. 4,569,967.
U.S. Pat. No. 4,883,666.
U.S. Pat. No. 4,968,733.
U.S. Pat. No. 4,976,859.
U.S. Pat. No. 5,082,670.
U.S. Pat. No. 5,084,350.
U.S. Pat. No. 5,158,881.
U.S. Pat. No. 5,284,761.
U.S. Pat. No. 5,364,769.
U.S. Pat. No. 5,514,774.
U.S. Pat. No. 5,534,615.
U.S. Pat. No. 5,545,723.
U.S. Pat. No. 5,550,050.
U.S. Pat. No. 5,591,821.
U.S. Pat. No. 5,618,531.
U.S. Pat. No. 5,633,347.
U.S. application Serial No. 08/785,534.
U.S. application Serial No. 09/061,026.
PCT Published Application WO 92/19195.
PCT Published Application WO 94/25503.
PCT Published Application WO 95/01203.
PCT Published Application WO 95/05452.
PCT Published Application WO 96/02286.
PCT Published Application WO 96/02646.
PCT Published Application WO 96/11698.
PCT Published Application WO 96/40871.
PCT Published Application WO 96/40959.
PCT Published Application WO 97/12635.

---

SEQUENCE LISTING

<160> NUMBER OF SEQ ID NOS: 13

<210> SEQ ID NO 1
<211> LENGTH: 16
<212> TYPE: PRT
<213> ORGANISM: Conus geographus
<220> FEATURE:
<221> NAME/KEY: PEPTIDE
<222> LOCATION: (1)..(13)
<223> OTHER INFORMATION: Xaa at residue 1 is pyro-Glu; Xaa at residue 13
      is Pro or hydroxy-Pro; Thr at residue 10 is modified to contain an
      O-glycan.

<400> SEQUENCE: 1

Xaa Ser Glu Glu Gly Gly Ser Asn Ala Thr Lys Lys Xaa Tyr Ile Leu
 1               5                  10                  15

<210> SEQ ID NO 2
<211> LENGTH: 16
<212> TYPE: PRT
<213> ORGANISM: Artificial Sequence
<220> FEATURE:
<223> OTHER INFORMATION: Description of Artificial Sequence:Generic
      Contulakin-G formula
<220> FEATURE:
<221> NAME/KEY: PEPTIDE
<222> LOCATION: (1)..(7)
<223> OTHER INFORMATION: Xaa at residue 1 is pyro-Glu, Glu, Gln or
      gamma-carboxy-Glu; Xaa at residues 2 and 7 is Ser,
      Thr, or S-glycan modified Cys; Xaa at residues 3
      and 4 is Glu or gamma-carboxy-Glu.
<220> FEATURE:
<221> NAME/KEY: PEPTIDE
<222> LOCATION: (8)..(10)
<223> OTHER INFORMATION: Xaa at residue 8 is Asn, N-glycan modified Asn
      or S-modified Cys; Xaa at residue 9 is Ala or Gly;
      Xaa at residue 10 is Thr, Ser, S-glycan modified
      Cys, Tyr or unnatural hydroxy containing amino
<220> FEATURE:

```
<221> NAME/KEY: PEPTIDE
<222> LOCATION: (11)..(12)
<223> OTHER INFORMATION: Xaa at residue 11 is Lys, N-methyl-Lys,
      N,N-dimethyl Lys, N,N,N-trimethyl Lys, Arg,
      ornithine, homo-Arg, or any unnatural basic amino
      acid; Xaa at residue 12 is Ala, Gly, Lys,
<220> FEATURE:
<221> NAME/KEY: PEPTIDE
<222> LOCATION: (12)..(13)
<223> OTHER INFORMATION: N,N-dimethyl-Lys, N,N,N-trimethyl-Lys, Arg,
      ornithine, homo-Arg, any unnatural basic amino
      acid or X-Lys; Xaa 13 is Pro or hydroxy-Pro.
<220> FEATURE:
<221> NAME/KEY: PEPTIDE
<222> LOCATION: (14)
<223> OTHER INFORMATION: Xaa at residue 14 is Tyr, mono-iodo-Tyr,
      di-iodo-Tyr, O-sulpho-Tyr, O-phospho-Tyr,
      nitro-Tyr, Trp, D-Trp, halo-Trp, halo-D-Trp, Phe,
      L-neo-Trp or unnatural aromatic amino acid, halo

<400> SEQUENCE: 2

Xaa Xaa Xaa Xaa Gly Gly Xaa Xaa Xaa Xaa Xaa Xaa Xaa Ile Leu
 1               5                  10                  15

<210> SEQ ID NO 3
<211> LENGTH: 17
<212> TYPE: DNA
<213> ORGANISM: Conus geographus
<220> FEATURE:
<221> NAME/KEY: misc_feature
<222> LOCATION: (1)..(17)
<223> OTHER INFORMATION: n is any nucleotide

<400> SEQUENCE: 3
atratnggyt tyttngt                                              17

<210> SEQ ID NO 4
<211> LENGTH: 15
<212> TYPE: PRT
<213> ORGANISM: Conus geographus
<220> FEATURE:
<221> NAME/KEY: PEPTIDE
<222> LOCATION: (9)
<223> OTHER INFORMATION: Xaa at residue 9 is unknown

<400> SEQUENCE: 4

Ser Glu Glu Gly Gly Ser Asn Ala Xaa Lys Lys Pro Tyr Ile Leu
 1               5                  10                  15

<210> SEQ ID NO 5
<211> LENGTH: 231
<212> TYPE: DNA
<213> ORGANISM: Conus geographus
<220> FEATURE:
<221> NAME/KEY: CDS
<222> LOCATION: (1)..(228)

<400> SEQUENCE: 5 atg cag acg gcc tac tgg gtg atg gtg atg atg atg gtg tgg att gca      48
Met Gln Thr Ala Tyr Trp Val Met Val Met Met Met Val Trp Ile Ala
 1               5                  10                  15 gcc cct ctg tct gaa ggt ggt aaa ctg aac gat gta att cgg ggt ttg      96
Ala Pro Leu Ser Glu Gly Gly Lys Leu Asn Asp Val Ile Arg Gly Leu
                20                  25                  30 gtg cca gac gac ata acc cca cag ctc atg ttg gga agt ctg att tcc     144
Val Pro Asp Asp Ile Thr Pro Gln Leu Met Leu Gly Ser Leu Ile Ser
            35                  40                  45 cgt cgt caa tcg gaa gag ggt ggt tca aat gca acc aag aaa ccc tat     192
Arg Arg Gln Ser Glu Glu Gly Gly Ser Asn Ala Thr Lys Lys Pro Tyr
```

```
           50                  55                  60
att cta agg gcc agc gac cag gtt gca tct ggg cca tag                  231
Ile Leu Arg Ala Ser Asp Gln Val Ala Ser Gly Pro
 65                  70                  75
```

<210> SEQ ID NO 6
<211> LENGTH: 76
<212> TYPE: PRT
<213> ORGANISM: Conus geographus

<400> SEQUENCE: 6

```
Met Gln Thr Ala Tyr Trp Val Met Val Met Met Val Trp Ile Ala
 1               5                  10                  15

Ala Pro Leu Ser Glu Gly Gly Lys Leu Asn Asp Val Ile Arg Gly Leu
                20                  25                  30

Val Pro Asp Asp Ile Thr Pro Gln Leu Met Leu Gly Ser Leu Ile Ser
            35                  40                  45

Arg Arg Gln Ser Glu Glu Gly Gly Ser Asn Ala Thr Lys Lys Pro Tyr
        50                  55                  60

Ile Leu Arg Ala Ser Asp Gln Val Ala Ser Gly Pro
 65                  70                  75
```

<210> SEQ ID NO 7
<211> LENGTH: 16
<212> TYPE: PRT
<213> ORGANISM: Conus geographus
<220> FEATURE:
<221> NAME/KEY: PEPTIDE
<222> LOCATION: (1)..(10)
<223> OTHER INFORMATION: Xaa at residue 1 is pyro-Glu; Thr at residue 10
      contains an O-glycan.

<400> SEQUENCE: 7

```
Xaa Ser Glu Glu Gly Gly Glu Asn Ala Thr Lys Lys Pro Tyr Ile Leu
 1               5                  10                  15
```

<210> SEQ ID NO 8
<211> LENGTH: 13
<212> TYPE: PRT
<213> ORGANISM: Bos sp.
<220> FEATURE:
<221> NAME/KEY: PEPTIDE
<222> LOCATION: (1)
<223> OTHER INFORMATION: Xaa at residue 1 is pyro-Glu.

<400> SEQUENCE: 8

```
Xaa Leu Tyr Glu Asn Lys Pro Arg Arg Pro Tyr Ile Leu
 1               5                  10
```

<210> SEQ ID NO 9
<211> LENGTH: 6
<212> TYPE: PRT
<213> ORGANISM: porcine

<400> SEQUENCE: 9

```
Lys Ile Pro Tyr Ile Leu
 1               5
```

<210> SEQ ID NO 10
<211> LENGTH: 8
<212> TYPE: PRT
<213> ORGANISM: Xenopus laevis

<400> SEQUENCE: 10

```
-continued

Gln Gly Lys Arg Pro Trp Ile Leu
 1               5

<210> SEQ ID NO 11
<211> LENGTH: 25
<212> TYPE: PRT
<213> ORGANISM: Homo sapiens

<400> SEQUENCE: 11

Met Leu Thr Lys Phe Glu Thr Lys Ser Ala Arg Val Lys Gly Leu Ser
 1               5                  10                  15

Phe His Pro Lys Arg Pro Trp Ile Leu
                20                  25

<210> SEQ ID NO 12
<211> LENGTH: 17
<212> TYPE: PRT
<213> ORGANISM: Vespula maculifrons

<400> SEQUENCE: 12

Thr Ala Thr Thr Arg Arg Arg Gly Arg Pro Pro Gly Phe Ser Pro Phe
 1               5                  10                  15

Arg

<210> SEQ ID NO 13
<211> LENGTH: 9
<212> TYPE: PRT
<213> ORGANISM: Homo sapiens

<400> SEQUENCE: 13

Arg Pro Pro Gly Phe Ser Pro Phe Arg
 1               5
```

What is claimed is:

1. A method for treating a disorder in an individual which comprises administering a therapeutically effective amount of an active agent to an individual in need of treatment of the disorder to effect treatment of said disorder, said disorder selected from the group consisting of seizure, epilepsy, convulsion, and psychosis, said active agent selected from the group consisting of:
   (a) contulakin-G comprising the amino acid sequence $Xaa_1$-Ser-Glu-Glu-Gly-Gly-Ser-Asn-Ala-Thr-Lys-Lys-$Xaa_2$-Tyr-Ile-Leu (SEQ ID NO: 1), where $Xaa_1$ is pyro-Glu, $Xaa_2$ is proline or hydroxyproline and $T_{10}$ is modified to contain an O-glycan;
   (b) a generic contulakin-G having the following general formula $Xaa_1$-$Xaa_2$-$Xaa_3$-$Xaa_3$-Gly-Gly-$Xaa_2$-$Xaa_4$-$Xaa_5$-$Xaa_6$-$Xaa_7$-$Xaa_8$-$Xaa_7$-$Xaa_9$-$Xaa_{10}$-Ile-Leu (SEQ ID NO:2), where $Xaa_1$ is pyro-Glu, Glu, Gln or γ-carboxy-Glu; $Xaa_2$ is Ser, Thr or S-glycan modified Cys; $Xaa_3$ is Glu or γ-carboxy-Glu; $Xaa_4$ is Asn, N-glycan modified Asn or S-glycan modified Cys; $Xaa_5$ is Ala or Gly; $Xaa_6$ is Thr, O-glycan modified Thr, Ser, O-glycan modified Ser, S-glycan modified Cys, Tyr or any hydroxy containing unnatural amino acid; $Xaa_7$ is Lys, N-methyl-Lys, N,N-dimethyl-Lys, N,N,N-trimethyl-Lys, Arg, ornithine, homoarginine or any unnatural basic amino acid; $Xaa_8$ is Ala, Gly, Lys, N-methyl-Lys, N,N-dimethyl-Lys, N,N,N-trimethyl-Lys, Arg, ornithine, homoarginine, any unnatural basic amino acid or X-Lys where X is $(CH_2)n$, phenyl, —$(CH_2)_m$—(CH=CH)—$(CH_2)_m$H or —$(CH_2)_m$—(C≡C)—$(CH_2)_m$H in which n is 1–4 and m is 0–2; $Xaa_9$ is Pro or hydroxy-Pro; and $Xaa_{10}$ is Tyr, mono-iodo-Tyr, di-iodo-Tyr, O-sulpho-Tyr, O-phospho-Tyr, nitro-Tyr, Trp, D-Trp, bromo-Trp, bromo-D-Trp, chloro-Trp, chloro-D-Trp, Phe, L-neo-Trp, or any unnatural aromatic amino acid, with the proviso that the generic contulakin-G is not desglycosylated contulakin-G;
   (c) a generic contulakin-G of (b) which is modified to contain an O-glycan, an S-glycan or an N-glycan;
   (d) a contulakin-G analog which comprises an N-terminal truncation of from 1 to 9 amino acids of the generic contulakin-G of (b);
   (e) a contulakin-G analog of (c), wherein an Ser-O-glycan, Thr-O-glycan or Cys-S-glycan is substituted for the amino acid residue at the truncated N-terminus;
   (f) a contulakin-G analog of (c), wherein an Ser-O-glycan, Thr-O-glycan or Cys-S-glycan is substituted for a residue at positions 2–9 of the generic contulakin-G; and
   (g) a contulakin-G analog which comprises an N-terminal truncation of 10 amino acids of the generic contulakin-G of (b) which is further modified to contain a Lys-N-glycan at residue 11 of the generic contulakin-G.

2. The method of claim 1 wherein the glycan is Gal(β1→3)GalNAc(α1→).

3. The method of claim 1 wherein the glycan has the structure shown in FIG. 3, wherein $R_1$ is an amino capable of being derivatized with a gylcan either chemically or enzymatically; $R_2$ is OH, $NH_2$, $NHSO_3Na$, NHAc, O-sulphate, O-phosphate, or O-glycan; $R_3$ is H, $SO_3$, $PO_3$, acetyl, sialic acid or monosaccharide; $R_4$ is H, $SO_3$, $PO_3$, acetyl or monosaccharide; $R_5$ is OH, $NH_2$, $NHSO_3Na$, NHAc, O-sulphate, O-phosphate, O-monosaccharide or, O-acetyl; $R_6$ is H, $SO_3$, $PO_3$, $SO_3$, $PO_3$, acetyl or monosaccharide; $R_7$ is H, $SO_3$, $PO_3$, acetyl or monosaccharide; $R_8$ is H, acetyl or monosaccharide; n is 0–4 and m is 1–4.

4. The method of claim 1, wherein said disorder is epilepsy, seizures or convulsions.

* * * * *

UNITED STATES PATENT AND TRADEMARK OFFICE
CERTIFICATE OF CORRECTION

PATENT NO.    : 6,696,408 B1
DATED         : February 24, 2004
INVENTOR(S)   : Craig et al.

It is certified that error appears in the above-identified patent and that said Letters Patent is hereby corrected as shown below:

Title page,
Item [75], Inventors, delete the following:
"A. Grey Craig, David Griffen, Maren Watkins, David R. Hillyard, Julita Imperial, Lourdes J. Cruz".

Column 6,
Line 36, insert -- acid -- after "amino".

Column 37,
Line 15, should read:

<223> OTHER INFORMATION: Xaa at residue 8 is Asn, N-glycan modified Asn
or S-modified Cys; Xaa at residue 9 is Ala or Gly;
Xaa at residue 10 is Thr, Ser, S-glycan modified
Cys, Tyr or unnatural hydroxy containing amino <u>acid</u>.

Line 24, should read:

<223> OTHER INFORMATION: Xaa at residue 11 is Lys, N-methyl-Lys,
N, N-dimethyl-Lys, N,N,N-trimethyl-Lys, Arg,
ornithine, homo-Arg, or any unnatural basic amino
acid; Xaa 12 is Ala, Gly, Lys, <u>N-methyl-Lys,</u>

Column 39,
Line 27, should read:

<223> OTHER INFORMATION: N, N-dimethyl-Lys, N,N,N-trimethyl-Lys, Arg,
ornithine, homo-Arg, any unnatural basic amino
acid or X-Lys <u>where X is $(CH_2)_n$, phenyl, $-(CH_2)_m-(CH=CH)-(CH_2)_n H$ or $-(CH_2)_m$ $-(C \equiv C)-(CH_2)_n H$ in which n is 1-4 and m is 0-2</u>; Xaa 13 is Pro or hydroxy-Pro.

Line 38, should read:

<223> OTHER INFORMATION: Xaa at residue 14 is Tyr, mono-iodo-Tyr,
di-iodo-Tyr, O-sulpho-Tyr, O-phospho-Tyr,
nitro-Tyr, Trp, D-Trp, halo-Trp, halo-D-Trp, Phe,
L-neo-Trp or unnatural aromatic amino acid, halo <u>is Br or Cl.</u>

UNITED STATES PATENT AND TRADEMARK OFFICE
CERTIFICATE OF CORRECTION

PATENT NO. : 6,696,408 B1
DATED : February 24, 2004
INVENTOR(S) : Craig et al.

It is certified that error appears in the above-identified patent and that said Letters Patent is hereby corrected as shown below:

<u>Column 41,</u>
Line 49, "$T_{1O}$" should read -- $T_{10}$ --;
Line 53, delete the second occurrence of "$Xaa_7$-".

<u>Column 42,</u>
Line 38, "(C=C)" should read -- (C≡C) --;
Line 52, "(c)" should read -- (d) --;
Line 66, insert -- acid -- after "amino".

Signed and Sealed this

Seventh Day of March, 2006

JON W. DUDAS
*Director of the United States Patent and Trademark Office*